United States Patent
Superak et al.

(10) Patent No.: US 8,609,928 B2
(45) Date of Patent: Dec. 17, 2013

(54) SQUASH LEAF CURL VIRUS (SLCV) RESISTANCE IN CUCURBITS

(75) Inventors: Ted Superak, Davis, CA (US); Julie Fauve, Nimes (FR); Eric Lionneton, Bouchemaine (FR); Maria Petronella Christina Sengers, Veghel (NL)

(73) Assignee: Vilmorin & Cie, Paris (FR)

( * ) Notice: Subject to any disclaimer, the term of this patent is extended or adjusted under 35 U.S.C. 154(b) by 413 days.

(21) Appl. No.: 12/836,888

(22) Filed: Jul. 15, 2010

(65) Prior Publication Data

US 2012/0017291 A1    Jan. 19, 2012

(51) Int. Cl.
*A01H 1/04* (2006.01)
*A01H 1/02* (2006.01)
*A01H 5/08* (2006.01)

(52) U.S. Cl.
USPC ........... 800/267; 800/265; 800/269; 800/266; 800/310; 435/6.11

(58) Field of Classification Search
USPC ....................................................... 800/310
See application file for complete search history.

(56) References Cited

U.S. PATENT DOCUMENTS

| 7,432,420 B2 | 10/2008 | Johnson et al. |
| 2007/0056059 A1 | 3/2007 | Johnson et al. |
| 2008/0313755 A1 | 12/2008 | Johnson |
| 2008/0320614 A1 | 12/2008 | Johnson et al. |

OTHER PUBLICATIONS

Garcia-Cano et al., "Phenotypic Expression, Stability, and Inheritance of a Recessive Resistance to Monopartite Begomoviruses Associated with Tomato Yellow Leaf Curl Disease in Tomato", *Virology*, 2008, online publication No. doi:10.1094/PHYTO-98-5-0618.
International Search Report based on International Patent Application No. PCT/US2011/043654, mailed on Nov. 21, 2011.
Written Opinion of the International Searching authority based on International Patent Application No. PCT/US2011/043654, mailed on Nov. 21, 2011.

*Primary Examiner* — David T Fox
*Assistant Examiner* — Jared Shapiro
(74) *Attorney, Agent, or Firm* — Cooley LLP

(57) ABSTRACT

The invention provides a new Squash Leaf Curl Virus (SLCV) resistant gene slc-2 in cucurbit plants and plants comprising the slc-2 gene. The invention also provides molecular markers linked to slc-2 gene. The invention further provides methods of breeding to produce plants that are resistant to SLCV, and the resistant plants produced by such methods.

4 Claims, 2 Drawing Sheets

FIGURE 1

SLCV allelism test

| variety | reistant | Intermediate | Susceptible | Total plants |
|---|---|---|---|---|
| Waltham butternut | 1 | 1 | 10 | 12 |
| Ns | 10 | 2 | 0 | 12 |
| CT4 | 8 | 3 | 0 | 11 |
| Subtotal resistant checks | 18 | 5 | 0 | |
| % total | 78 | 22 | 0 | |
| NsCT3 | 6 | 4 | 2 | 12 |
| NsCT3 | 9 | 4 | 0 | 13 |
| NsCT3 | 10 | 1 | 0 | 11 |
| Subtotal Ns x CT3 F2 | 25 | 9 | 2 | 36 |
| % total | 69 | 25 | 6 | |
| Waltham butternut | 1 | 3 | 8 | 12 |
| NsCT4 | 11 | 0 | 0 | 11 |
| NsCT4 | 10 | 2 | 0 | 12 |
| NsCT4 | 8 | 4 | 0 | 12 |
| NsCT4 | 8 | 2 | 0 | 10 |
| Subtotal Ns x CT4 F2 | 37 | 8 | 0 | 45 |
| % total | 82 | 18 | 0 | |
| Waltham butternut | 0 | 0 | 11 | 11 |
| Subtotal susceptible checks | 2 | 4 | 29 | 35 |
| % total | 6 | 11 | 83 | |

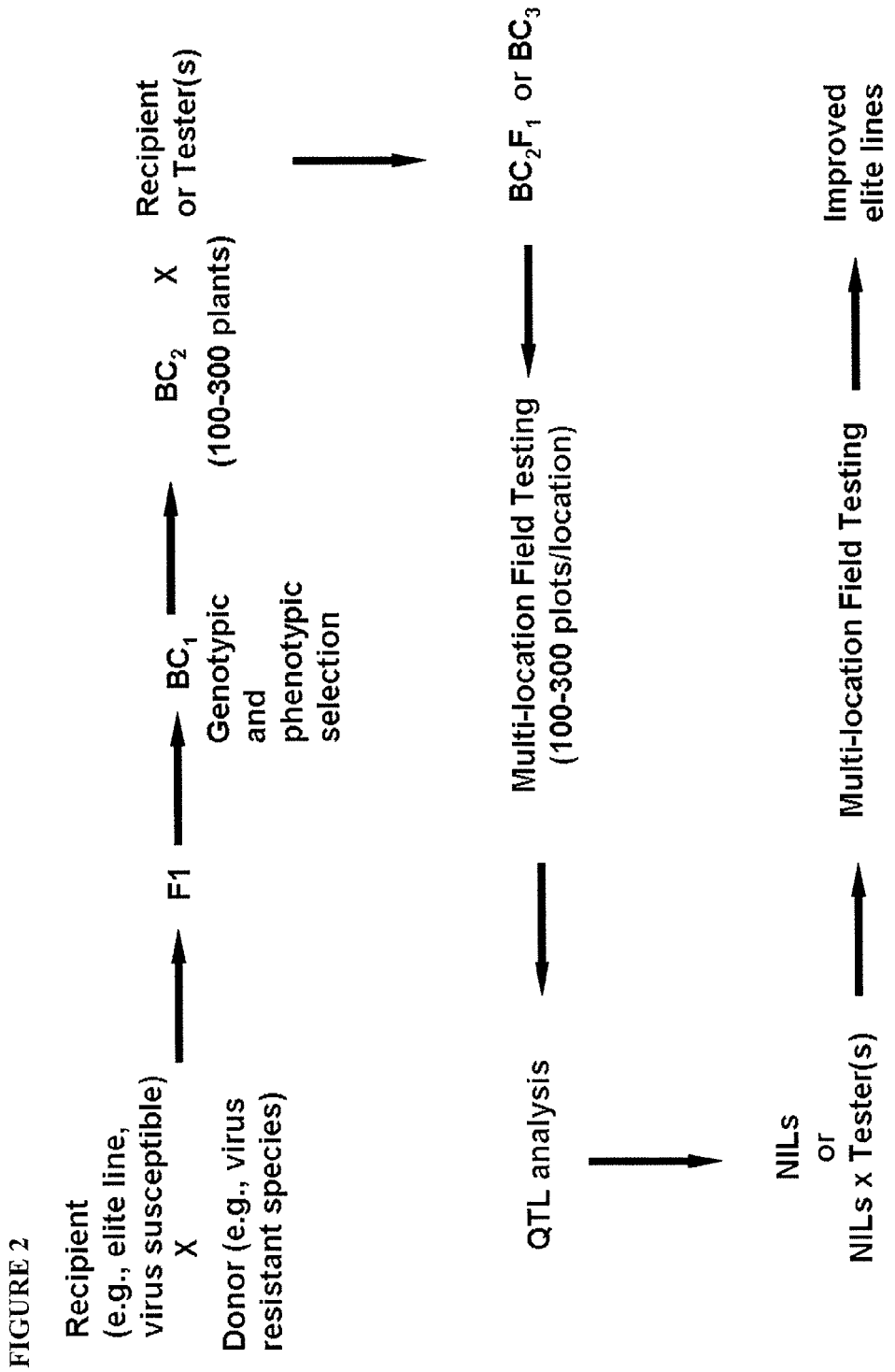

SQUASH LEAF CURL VIRUS (SLCV) RESISTANCE IN CUCURBITS

TECHNICAL FIELD

The application relates to a novel Squash Leaf Curl Virus (SLCV) resistance gene identified in *Cucurbita moschata* plants; non-*C. moschata* cucurbit plants, including inbred plants and hybrid plants, having said resistance gene; molecular markers associated with the resistance gene; methods of developing plants with resistance to SLCV and plants developed by such methods.

BACKGROUND

Cucurbitaceae is a plant family commonly known as melons, gourds or cucurbits and includes crops like cucumbers, squashes (including pumpkins), luffas, melons and watermelons. According to Food and Agriculture Organization (FAO, 2002), world production of watermelon exceeded 80 million tons; cucumber exceeded 36 million tons; melon exceeded 22 million tons; and squash exceeded 17 million tons.

A variety of pathogens (virus, fungi, bacteria, nematodes, and insects) affect the productivity of cucurbits (Blanchard et al., 1994 A color atlas of cucurbit diseases, New York: Manson Publishing/John Wiley; Zitter et al., 1996 Compendium of cucurbit diseases, St Paul, Minn., APS Press). Cucurbits are susceptible to many viruses and virus resistance is therefore of major agricultural importance (Provvidenti, 1993, Resistance to viral disease of cucurbits, In Kyle, M. M., ed. *Resistance to viral diseases of vegetables*, Portland, Oreg., Timber Press, 1993: 8-43).

The taxonomic family Geminiviridae includes some of the most important plant viruses causing severe diseases in agricultural, ornamental and horticultural crops. During the last three decades numerous whitefly-transmitted Begomoviruses, a genus of geminivirus, have emerged as devastating pathogens, particularly in the tropics and subtropics, causing huge economic losses and threatening crop production. Squash Leaf Curl Virus (SLCV), a begomovirus, can cause severe losses in many areas of squash production, but particularly in the major squash growing areas of Mexico, Arizona, California and the Middle East. SLCV was first observed in squash in California during 1977 and 1978 (Flock R A, Mayhew Del., 1981 Squash leaf curl, a new disease of cucurbits in California, *Plant Dis.* 65:75-76) and in cultivated buffalo gourd in Arizona at about the same time (Rosemeyer et al., 1986 Five viruses isolated from field-grown buffalo gourd, *Cucurbita foetidissima* HBK, a potential crop for semi-arid lands, *Plant Dis* 70:405-409).

Current methods of preventing and controlling geminivirus include controlling the spread of insect vectors that carry the virus, developing transgenic plants expressing the viral coat protein, and using classical breeding methods to develop plants having natural resistance to the virus. Disease resistant plants developed using classical plant breeding offer an effective, safe, and relatively less expensive method of controlling many crop diseases. For example, U.S. Pat. No. 7,432,420 describes a squash plant with resistance to SLCV due to a dominant resistance gene in the squash genome.

The present invention provides cucurbit plants, including squash plants, which have an important, useful and alternative form of resistance to SLCV. The resistance of the present invention is imparted by the newly discovered recessive gene slc-2.

SUMMARY

The present invention provides non-*Cucurbita moschata* cucurbit seeds whose genome contains at least one copy of a recessive allele of a slc-2 gene coding for resistance to Squash Leaf Curl Virus (SLCV), said at least one allele being present in the seeds deposited as NCIMB Accession No. 41728. In one embodiment, the genome of the non-*C. moschata* cucurbit seeds contain two copies of the recessive alleles of the slc-2 gene. The present invention also provides plants, explants, scions, cuttings, seeds, fruit, rootstock, pollen, ovules, and/or plant parts produced by growing said non-*Cucurbita moschata* cucurbit seeds. In some embodiments, the cucurbit plants are squash plants, including genetically related squash populations comprising such squash plants. The present invention also provides tissue cultures of regenerable cells of the non-*C. moshata* cucurbit plants of the present invention, wherein the regenerable cells are derived from embryos, protoplasts, meristematic cells, callus, pollen, leaves, anthers, stems, petioles, roots, root tips, fruits, seeds, flowers, cotyledons, and/or hypocotyls.

The present invention also provides methods for producing a cucurbit seed that can grow into a cucurbit plant comprising at least one recessive allele of a slc-2 gene, said methods comprising growing non-*Cucurbita moschata* cucurbit seeds whose genome contains at least one copy of a recessive allele of a slc-2 gene coding for resistance to Squash Leaf Curl Virus (SLCV), crossing the resultant cucurbit plants as the first parent plant with a second parent plant, and harvesting the resultant seed. In one embodiment, such methods comprise backcrossing to one of said parent plants for two or more generations. In another embodiment, such methods comprise selecting a plant having at least one copy of the recessive allele of the slc-2 gene in each generation. In another embodiment, the selection comprises molecular marker assisted selection, wherein the molecular marker assisted selection may comprise using any one of the molecular markers whose defining primers are listed in Table 8. In another embodiment, the second parent plant has one or more preferred economically important traits, such as resistance to one or more biotic and/or abiotic stresses. In yet another embodiment, such methods comprise selecting a plant having two copies of the recessive allele of the slc-2 gene in each generation.

The present invention also provides genetic markers linked with a slc-2 gene. In some embodiments, such genetic markers include restriction fragment length polymorphisms (RFLPs), isozyme markers, allele specific hybridization (ASH), amplified variable sequences of plant genome, self-sustained sequence replication, simple sequence repeat (SSR), and amplified fragment length polymorphisms (AFLPs). Some AFLP markers useful in the present invention are defined by the primers in Table 8. The present invention also provides methods of identifying a SLCV resistant cucurbit plant by identifying at least one genetic locus linked with the genetic markers of the present invention, wherein such methods comprise: (i) detecting the presence of at least one genetic locus in the plant, wherein the genetic locus localizes to a chromosome interval flanked on either side by one or more genetic markers of the present invention; and (ii) identifying the plant comprising the genetic locus. In some embodiments, such methods utilize a whole plant, a plant organ, a plant seed, or a plant cell for the identification. In one embodiment, the methods further comprise constructing a genetic linkage map of said plant using the genetic marker of the present invention.

The present invention also provides methods of introducing a slc-2 resistance gene into a recipient plant comprising crossing a non-*Cucurbita moschata* cucurbit plant whose genome contains at least one copy of a recessive allele of a slc-2 gene coding for resistance to Squash Leaf Curl Virus (SLCV) with the recipient plant and harvesting the resultant seed. In one embodiment the method further comprises backcrossing to said recipient plant for two or more generations. In another embodiment the methods further comprise selection for plants having slc-2 gene in each generation.

The present invention provides plants comprising said recessive slc-2 gene. In some embodiments, said plants are cucurbit plants. In one embodiment, said cucurbit plants are resistant to SLCV. In another embodiment, said cucurbit plants comprising the slc-2 gene do not express the resistance (e.g., cucurbit plants comprise heterologous slc-2 alleles). In further embodiments, said cucurbit plants are non-*C. moschata* cucurbit plants. In one embodiment, said cucurbit plants are produced from the cucurbit seeds containing the recessive gene slc-2. In other embodiments, new cucurbit plants can be derived from a cross wherein at least one parent comprises the recessive gene slc-2 as described above. The parent comprising the recessive gene slc-2 can be either resistant to SLCV, or susceptible to SLCV (e.g., due to heterologous alleles). In one embodiment, the presence of the recessive slc-2 gene in the cucurbit plant is characterized by at least one molecular marker which defining primers are in Table 8. In one embodiment, the invention further provides cucurbit plants having essentially all the morphological and physiological characteristics of the cucurbit plants as described above.

The present invention also provides a seed, a fruit, a plant population, a plant, a plant part, a plant cell derived from the plants comprising said recessive slc-2 gene as described above. In one embodiment, the invention provides an embryo, pollen and/or an ovule of the plants comprising said recessive slc-2 gene.

The present invention also provides a tissue culture of the regenerable cells of the plants comprising said recessive slc-2 gene, plant parts, plant tissue or plant cells, wherein said tissue culture retains the recessive slc-2 gene. In one embodiment, the regenerable cells are derived from embryos, protoplasts, meristematic cells, callus, pollen, leaves, anthers, stems, petioles, roots, root tips, fruits, seeds, flowers, cotyledons, or hypocotyls.

The present invention also provides a cutting, a rootstock, a scion, or an explant from the plants comprising said recessive slc-2 gene as described above.

The present invention also provides a progeny derived from the plants comprising said recessive slc-2 gene as described above, whether produced sexually or asexually, wherein said progeny retains resistance to SLCV. In one embodiment, at least 5% of said progeny is resistant to SLCV. For example, about 5% to about 15%, about 16% to about 25%, 26% to about 50%, 51% to about 99%, or more of said progeny are resistant to SLCV.

The present invention also provides genetic markers that are tightly linked to the slc-2 gene.

The present invention also provides a method of isolating a nucleic acid sequence designated as slc-2 gene conferring resistance to SLCV, comprising: a) crossing the SLCV resistant plant of the present invention as a donor with a suitable susceptible plant to produce offspring plants as a mapping population; b) challenging said offspring plants with said virus and determining the resistance in said offspring population; and c) cloning the slc-2 gene. In one embodiment, said cloning step comprises molecular marker assisted mapping and cloning.

The present invention also provides a method of identifying a SLCV resistant cucurbit plant by identifying the presence of slc-2 gene that is closely linked with the genetic markers as described above, the method comprises:

(i) detecting the presence of slc-2 gene in the plant, wherein the slc-2 gene localizes to a chromosome interval flanked on either side with one or more genetic markers as described above, and (ii) identifying the plant comprising the slc-2 gene.

The present invention also provides methods of producing a cucurbit seed, wherein the seed can grow into a plant resistant to SLCV. The methods comprise growing the SLCV resistant cucurbit plant of the present invention, crossing the SLCV resistant cucurbit plant as the first parent plant with a second parent plant, and harvesting the resultant seeds. In one embodiment, the methods comprise backcrossing to one of said parent plants for two or more generations. In further embodiments, the methods comprise selection for plants having slc-2 gene in each generation.

The present invention also provides a plant population, plant, plant part, plant tissue, or plant cell that is resistance to SLCV, wherein the plant population, plant, plant part, plant tissue, or plant cell is produced by transferring the slc-2 gene conferring resistance to SLCV, and/or one or more other QTLs contributing to the resistance, to a plant population, plant, plant part, plant tissue, or plant cell of a recipient. In one embodiment, the slc-2 gene and/or one or more other QTLs can be transferred by breeding methods. In one embodiment, said breeding method comprises using an introgression line library. In one embodiment, said method comprises constructing a genetic linkage map of said plant using the genetic markers as described above. In further embodiments, said method further comprises backcrossing to said recipient plant for two or more generations.

BRIEF DESCRIPTION OF THE DRAWINGS

FIG. 1 depicts results of allelism analysis of SLCV resistant plants Ns, CT3 and CT4 of the present invention.

FIG. 2 depicts exemplary scheme of the Advanced Backcross QTL mapping strategy.

DESCRIPTION OF THE TEXT FILE SUBMITTED ELECTRONICALLY

The contents of the text file submitted electronically are incorporated herein by reference in their entirety: A computer readable format copy of the Sequence Listing (filename: VILM00200US.txt, date recorded: Jul. 15, 2010, file size 5 kilobytes).

DETAILED DESCRIPTION

All publications, patents and patent applications, including any drawings and appendices, herein are incorporated by reference to the same extent as if each individual publication or patent application was specifically and individually indicated to be incorporated by reference.

The following description includes information that may be useful in understanding the present invention. It is not an admission that any of the information provided herein is prior art or relevant to the presently claimed inventions, or that any publication specifically or implicitly referenced is prior art.

Definitions

As used herein, the verb "comprise" as is used in this description and in the claims and its conjugations are used in its non-limiting sense to mean that items following the word are included, but items not specifically mentioned are not excluded.

As used herein, the term "plant" refers to any living organism belonging to the kingdom Plantae (i.e., any genus/species in the Plant Kingdom).

As used herein, the term "plant part" refers to any part of a plant including but not limited to the shoot, root, stem, seeds, stipules, leaves, petals, flowers, ovules, bracts, branches, petioles, internodes, bark, pubescence, tillers, rhizomes, fronds, blades, pollen, stamen, and the like. The two main parts of plants grown in some sort of media, such as soil, are often referred to as the "above-ground" part, also often referred to as the "shoots", and the "below-ground" part, also often referred to as the "roots".

The term "a" or "an" refers to one or more of that entity; for example, "a gene" refers to one or more genes or at least one gene. As such, the terms "a" (or "an"), "one or more" and "at least one" are used interchangeably herein. In addition, reference to "an element" by the indefinite article "a" or "an" does not exclude the possibility that more than one of the elements are present, unless the context clearly requires that there is one and only one of the elements.

As used herein, the term "nucleic acid" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The term "nucleic acid" and "nucleotide sequence" are used interchangeably.

As used herein, the terms "polypeptide," "peptide," and "protein" are used interchangeably herein to refer to polymers of amino acids of any length. These terms also include proteins that are post-translationally modified through reactions that include glycosylation, acetylation and phosphorylation.

As used herein, the term "derived from" refers to the origin or source, and may include naturally occurring, recombinant, unpurified, or purified molecules. A nucleic acid or an amino acid derived from an origin or source may have all kinds of nucleotide changes or protein modification as defined elsewhere herein.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T en G/C content) of primer. A pair of bi-directional primers consists of one forward and one reverse primer as commonly used in the art of DNA amplification such as in PCR amplification.

As used herein, the term "resistant", or "resistance", describes a plant, line or cultivar that shows fewer or reduced symptoms to a biotic pest or pathogen than a susceptible (or more susceptible) plant, line or variety to that biotic pest or pathogen. These terms are variously applied to describe plants that show no symptoms as well as plants showing some symptoms but that are still able to produce marketable product with an acceptable yield. Some lines that are referred to as resistant are only so in the sense that they may still produce a crop, even though the plants may appear visually stunted and the yield is reduced from that of uninfected plants. As defined by the International Seed Federation (ISF), a non-governmental, non-profit organization representing the seed industry (see "Definition of the Terms Describing the Reaction of Plants to Pests or Pathogens and to Abiotic Stresses for the Vegetable Seed Industry", May 2005), the recognition of whether a plant is affected by or subject to a pest or pathogen can depend on the analytical method employed. Resistance is defined by the ISF as the ability of a plant types to restrict the growth and development of a specified pest or pathogen and/or the damage they cause when compared to susceptible plant varieties under similar environmental conditions and pest or pathogen pressure. Resistant plant types may still exhibit some disease symptoms or damage. Two levels of resistance are defined. The term "high/standard resistance" is used for plant varieties that highly restrict the growth and development of the specified pest or pathogen under normal pest or pathogen pressure when compared to susceptible varieties. "Moderate/intermediate resistance" is applied to plant types that restrict the growth and development of the specified pest or pathogen, but exhibit a greater range of symptoms or damage compared to plant types with high resistance. Plant types with intermediate resistance will show less severe symptoms than susceptible plant varieties, when grown under similar field conditions and pathogen pressure. Methods of evaluating resistance are well known to one skilled in the art. Such evaluation may be performed by visual observation of a plant or a plant part (e.g., leaves, roots, flowers, fruits et. al) in determining the severity of symptoms. For example, when each plant is given a resistance score on a scale of 1 to 5 based on the severity of the reaction or symptoms, with 5 being the resistance score applied to the most resistant plants (e.g., no symptoms, or with the least symptoms), and 1 the score applied to the plants with the most severe symptoms, then a line is rated as being resistant when at least 75% of the plants have a resistance score at a 3, 4, or 5 level, while susceptible lines are those having more than 25% of the plants scoring at a 1 or 2 level. If a more detailed visual evaluation is possible, then one can use a scale from 1 to 10 so as to broaden out the range of scores and thereby hopefully provide a greater scoring spread among the plants being evaluated. Alternative resistance score might be used, for example by focusing on certain symptoms such as the leaf curling of the plants: in such a case, a 0 would be attributed to plants showing no symptoms at all, 1 will be given to plants showing small curling on the older leaves, 2 for small curling on the older leaves and gauffrage (meaning kind of thickening of the leaf) on young leaves, 3 for small curling on young leaves, 4 for curling on young leaves and 5 for crispation (meaning downward and/or stunting) and curling on young leaves. Then a line is rated as being resistant when at least 75% of the plants have a resistance score at a 0, 1, or 2 level, while susceptible lines are those having more than 25% of the plants scoring at a 3, 4, or 5 level. In addition to such visual evaluations, the evaluation can also be performed by determining the virus bio-density in a plant or plant part using electron microscopy and/or through molecular biological methods, such as protein hybridization (e.g., ELISA, measuring viral protein density) and/or nucleic acid hybridization (e.g., RT-PCR, measuring viral RNA density). A plant is resistant to the virus strain, for example, if it has a virus RNA and/or protein density that is about 50%, about 40%, about 30%, about 20%, about 10%, about 5%, about 2%, about 1%, about 0.1%, about 0.01%, about 0.001%, or about 0.0001% of the RNA and/or protein density in a susceptible plant.

As used herein, the term "full resistance" is referred to as complete failure of the virus to develop after infection, and may either be the result of failure of the virus to enter the cell (no initial infection) or may be the result of failure of the virus to multiply in the cell and infect subsequent cells (no subliminal infection, no spread). The presence of full resistance may be determined by establishing the absence of viral particles or viral RNA in cells of the plant, as well as the absence of any disease symptoms in said plant, upon exposure of said plant to an infective dosage of virus (i.e. after 'infection'). Among breeders, this phenotype is often referred to as "immune". "Immunity" as used herein thus refers to a form of resistance characterized by absence of viral replication even when virus is actively transferred into cells by e.g. electroporation.

As used herein, the term "partial resistance" is referred to as reduced multiplication of the virus in the cell, as reduced (systemic) movement of the virus, and/or as reduced symptom development after infection. The presence of partial resistance may be determined by establishing the systemic presence of low titres of viral particles or viral RNA in the plant and the presence of decreased or delayed disease-symptoms in said plant upon exposure of said plant to an infective dosage of virus. Virus titres may be determined by using a quantitative detection method (e.g. an ELISA method or a quantitative reverse transcriptase-polymerase chain reaction (RT-PCR)). Among breeders, this phenotype is often referred to as "intermediate resistant."

As used herein, the term "hypersensitive" refers to a form of resistance whereby the infection remains local and does not systemically spread, for instance due to local necrosis of infected tissue or lack of systemic movement beyond inoculated tissue. Hypersensitive plants show local, but severe disease symptoms and the local presence of the virus can be established in such plants.

As used herein, the term "tolerant" is used herein to indicate a phenotype of a plant wherein disease-symptoms remain absent upon exposure of said plant to an infective dosage of virus, whereby the presence of a systemic or local viral infection, virus multiplication, at least the presence of viral genomic sequences in cells of said plant and/or genomic integration thereof can be established. Tolerant plants are therefore resistant for symptom expression but symptomless carriers of the virus. Sometimes, viral sequences may be present or even multiply in plants without causing disease symptoms. This phenomenon is also known as "latent infection". Some DNA and RNA viruses, may become undetectable following a primary infection only to reappear later and produce acute disease. In latent infections, the virus may exist in a truly latent non-infectious occult form, possibly as an integrated genome or an episomal agent (so that viral particles cannot be found in the cytoplasm, while PCR protocols may indicate the present of viral nucleic acid sequences) or as an infectious and continuously replicating agent. A reactivated virus may spread and initiate an epidemic among susceptible contacts. The presence of a "latent infection" is indistinguishable from the presence of a "tolerant" phenotype in a plant.

As used herein, the term "susceptible" is used herein to refer to a plant having no or virtually no resistance to the virus resulting in entry of the virus into the plant's cells and multiplication and systemic spread of virus, resulting in disease symptoms. The term "susceptible" is therefore equivalent to "non-resistant". A susceptible plant exhibits normal virus titres in its cells upon infection. Susceptibility may thus be determined by establishing the presence of normal (i.e. relative to other viral infections in plants) titres of viral particles or of viral RNA in cells of the plant and the presence of normal disease symptoms in said plant upon exposure of said plant to an infective dosage of virus.

As used herein, the term "sensitive" reflects the symptomatic reaction of a susceptible plant upon virus infection. The reaction or symptoms can be more or less severe depending on the level of sensitivity of the plant. If the plant is injured or even killed by the virus, said plant is qualified as "sensitive".

As used herein the term "SLCV-resistant," is to be interpreted as referring to the resistance of a plant, plant tissue, or plant cell, in particular a cucurbit, to the establishment of an infection, or the establishment of SLCV.

As used herein, the term "sample" includes a sample from a plant, a plant part, a plant cell, or from a transmission vector, or a soil, water or air sample.

As used herein, the term "transmission vector" as used herein refers to the disease-spreading agent or substance.

As used herein, the term "offspring" refers to any plant resulting as progeny from a vegetative or sexual reproduction from one or more parent plants or descendants thereof. For instance an offspring plant may be obtained by cloning or selfing of a parent plant or by crossing two parents plants and include selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's, F2's etc. An F1 may thus be (and usually is) a hybrid resulting from a cross between two true breeding parents (true-breeding is homozygous for a trait), while an F2 may be (and usually is) an offspring resulting from self-pollination of said F1 hybrids.

As used herein, the term "cross", "crossing", "cross pollination" or "cross-breeding" refer to the process by which the pollen of one flower on one plant is applied (artificially or naturally) to the ovule (stigma) of a flower on another plant.

As used herein, the term "cultivar" refers to a variety, strain or race of plant that has been produced by horticultural or agronomic techniques and is not normally found in wild populations.

As used herein, the terms "dicotyledon" and "dicot" refer to a flowering plant having an embryo containing two seed halves or cotyledons. Examples include tobacco; tomato; the legumes, including peas, alfalfa, clover and soybeans; oaks; maples; roses; mints; squashes; daisies; walnuts; cacti; violets and buttercups.

As used herein, the term "gene" refers to any segment of DNA associated with a biological function. Thus, genes include, but are not limited to, coding sequences and/or the regulatory sequences required for their expression. Genes can also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "genotype" refers to the genetic makeup of an individual cell, cell culture, tissue, organism (e.g., a plant), or group of organisms.

As used herein, the term "hemizygous" refers to a cell, tissue or organism in which a gene is present only once in a genotype, as a gene in a haploid cell or organism, a sex-linked gene in the heterogametic sex, or a gene in a segment of chromosome in a diploid cell or organism where its partner segment has been deleted.

As used herein, the term "heterozygote" refers to a diploid or polyploid individual cell or plant having different alleles (forms of a given gene) present at least at one locus. As used herein, the term "heterozygous" refers to the presence of different alleles (forms of a given gene) at a particular gene locus.

As used herein, the terms "homolog" or "homologue" refer to a nucleic acid or peptide sequence which has a common origin and functions similarly to a nucleic acid or peptide sequence from another species.

As used herein, the term "homozygote" refers to an individual cell or plant having the same alleles at one or more loci.

As used herein, the term "homozygous" refers to the presence of identical alleles at one or more loci in homologous chromosomal segments.

As used herein, the term "hybrid" refers to any individual cell, tissue or plant resulting from a cross between parents that differ in one or more genes.

As used herein, the term "inbred" or "inbred line" refers to a relatively true-breeding strain.

The term "single allele converted plant" as used herein refers to those plants which are developed by a plant breeding technique called backcrossing wherein essentially all of the desired morphological and physiological characteristics of an inbred are recovered in addition to the single allele transferred into the inbred via the backcrossing technique.

As used herein, the term "line" is used broadly to include, but is not limited to, a group of plants vegetatively propagated from a single parent plant, via tissue culture techniques or a group of inbred plants which are genetically very similar due to descent from a common parent(s). A plant is said to "belong" to a particular line if it (a) is a primary transformant (T0) plant regenerated from material of that line; (b) has a pedigree comprised of a T0 plant of that line; or (c) is genetically very similar due to common ancestry (e.g., via inbreeding or selling). In this context, the term "pedigree" denotes the lineage of a plant, e.g. in terms of the sexual crosses affected such that a gene or a combination of genes, in heterozygous (hemizygous) or homozygous condition, imparts a desired trait to the plant.

As used herein, the term "locus" (plural: "loci") refers to any site that has been defined genetically. A locus may be a gene, or part of a gene, or a DNA sequence that has some regulatory role, and may be occupied by different sequences.

As used herein, the term "mass selection" refers to a form of selection in which individual plants are selected and the next generation propagated from the aggregate of their seeds.

As used herein, the term "monocotyledon" or "monocot" refer to any of a subclass (Monocotyledoneae) of flowering plants having an embryo containing only one seed leaf and usually having parallel-veined leaves, flower parts in multiples of three, and no secondary growth in stems and roots. Examples include lilies; orchids; rice; corn, grasses, such as tall fescue, goat grass, and Kentucky bluegrass; grains, such as wheat, oats and barley; irises; onions and palms.

As used herein, the term "open pollination" refers to a plant population that is freely exposed to some gene flow, as opposed to a closed one in which there is an effective barrier to gene flow.

As used herein, the tennis "open-pollinated population" or "open-pollinated variety" refer to plants normally capable of at least some cross-fertilization, selected to a standard, that may show variation but that also have one or more genotypic or phenotypic characteristics by which the population or the variety can be differentiated from others. A hybrid, which has no barriers to cross-pollination, is an open-pollinated population or an open-pollinated variety.

As used herein when discussing plants, the term "ovule" refers to the female gametophyte, whereas the term "pollen" means the male gametophyte.

As used herein, the term "phenotype" refers to the observable characters of an individual cell, cell culture, organism (e.g., a plant), or group of organisms which results from the interaction between that individual's genetic makeup (i.e., genotype) and the environment.

As used herein, the term "plant tissue" refers to any part of a plant. Examples of plant organs include, but are not limited to the leaf, stem, root, tuber, seed, branch, pubescence, nodule, leaf axil, flower, pollen, stamen, pistil, petal, peduncle, stalk, stigma, style, bract, fruit, trunk, carpel, sepal, anther, ovule, pedicel, needle, cone, rhizome, stolon, shoot, pericarp, endosperm, placenta, berry, stamen, and leaf sheath.

As used herein, the term "self-crossing", "self pollinated" or "self-pollination" means the pollen of one flower on one plant is applied (artificially or naturally) to the ovule (stigma) of the same or a different flower on the same plant.

As used herein, the term "variety" refers to a subdivision of a species, consisting of a group of individuals within the species that are distinct in form or function from other similar arrays of individuals.

As used herein, the term "QTL" is used herein in its art-recognized meaning. A QTL may for instance comprise one or more genes of which the products confer the genetic resistance. Alternatively, a QTL may for instance comprise regulatory genes or sequences of which the products influence the expression of genes on other loci in the genome of the plant thereby conferring the virus resistance. The QTLs of the present invention may be defined by indicating their genetic location in the genome of the respective virus-resistant accession using one or more molecular genomic markers. One or more markers, in turn, indicate a specific locus. Distances between loci are usually measured by frequency of crossing-over between loci on the same chromosome. The farther apart two loci are, the more likely that a crossover will occur between them. Conversely, if two loci are close together, a crossover is less likely to occur between them. As a rule, one centimorgan (cM) is equal to 1% recombination between loci (markers). When a QTL can be indicated by multiple markers the genetic distance between the end-point markers is indicative of the size of the QTL.

Plant Diseases Resistance

Plant disease resistance derives both from pre-foamed defenses and from infection-induced responses mediated by the plant immune system. Disease outcome is determined by the three-way interaction of the pathogen, the plant, and the environmental conditions (an interaction known as the disease triangle). Defense-activating compounds can move cell-to-cell and systemically through the plant vascular system, but plants do not have circulating immune cells so most cell types in plants retain the capacity to express a broad suite of antimicrobial defenses. Although obvious qualitative differences in disease resistance can be observed when some plants are compared (allowing classification as "resistant" or "susceptible" after infection by the same pathogen strain at similar pathogen pressure in similar environments), a gradation of quantitative differences in disease resistance is more typically observed between plant lines or genotypes.

Preformed structures and compounds that contribute to resistance in plants include, but are not limited to, plant cuticle/surface, plant cell walls, antimicrobial chemicals (e.g., glucosides, saponins), antimicrobial proteins, enzyme inhibitors, detoxifying enzymes that break down pathogen-derived toxins, receptors that perceive pathogen presence and active inducible plant defenses. Inducible plant defenses that are generated upon or after infection include, but are not limited to, cell wall reinforcement (e.g., increased callose, lignin, suberin, cell wall proteins), antimicrobial chemicals (e.g., reactive oxygen species such as hydrogen peroxide, peroxynitrite, or complex phytoalexins such as genistein or camalexin), antimicrobial proteins (e.g., defensins, thionins, or pathogenesis-related (PR) proteins), antimicrobial enzymes (e.g., chitinases, beta-glucanases, peroxidases), hypersensitive response (e.g., rapid host cell death response associated with defense mediated by resistance genes), and post-translation gene silencing.

Plant immune systems show some mechanistic similarities and apparent common origin with the immune systems of insects and mammals, but also exhibit many plant-specific characteristics. As in most cellular responses to the environment, defenses are activated when receptor proteins directly or indirectly detect pathogen presence and trigger ion channel gating, oxidative burst, cellular redox changes, protein kinase cascades, and/or other responses that either directly activate cellular changes (such as cell wall reinforcement), or activate changes in gene expression that then elevate plant defense responses.

Plants, like animals, have a basal immune system that includes a small number of pattern recognition receptors that are specific for broadly conserved microbe-associated molecular patterns (MAMPs, also called pathogen-associated molecular patterns or PAMPs). Examples of these microbial compounds that elicit plant basal defense include bacterial flagellin or lipopolysaccharides, or fungal chitin. The defenses induced by MAMP perception are sufficient to repel most potentially pathogenic microorganisms. However, pathogens express effector proteins that are adapted to allow them to infect certain plant species; these effectors often enhance pathogen virulence by suppressing basal host defenses.

Importantly, plants have evolved R genes (resistance genes) whose products allow recognition of specific pathogen effectors, either through direct binding of the effector or by recognition of the alteration that the effector has caused to a host protein. R gene products control a broad set of disease resistance responses whose induction is often sufficiently rapid and strong to stop adapted pathogens from further growth or spread. Plant genomes each contain a few hundred apparent R genes, and the R genes studied to date usually confer specificity for particular strains of a pathogen species. As first noted by Harold Flor in the mid-20th century in his formulation of the gene-for-gene relationship, the plant R gene and the pathogen "avirulence gene" (effector gene) must have matched specificity for that R gene to confer resistance. The presence of an R gene can place significant selective pressure on the pathogen to alter or delete the corresponding avirulence/effector gene. Some R genes show evidence of high stability over millions of years while other R genes, especially those that occur in small clusters of similar genes, can evolve new pathogen specificities over much shorter time periods.

The use of receptors carrying leucine-rich repeat (LRR) pathogen recognition specificity domains is common to plant, insect, jawless vertebrate and mammal immune systems, as is the presence of Toll/Interleukin receptor (TIR) domains in many of these receptors, and the expression of defensins, thionins, oxidative burst and other defense responses (Jones and Dangl. 2006 The plant immune system. *Nature* 444:323-329. Ting et al. 2008. NLRs at the intersection of cell death and immunity. *Nat Rev Immunol.* 8:372-379. which are incorporated herein by reference in their entireties).

Some of the key endogenous chemical mediators of plant defense signal transduction include salicylic acid, jasmonic acid or jasmonate, ethylene, reactive oxygen species, and nitric oxide. Numerous genes and/or proteins have been identified that mediate plant defense signal transduction (Hammond-Kosack and Parker, 2003, Deciphering plant-pathogen communication: fresh perspectives for molecular resistance breeding. *Curr. Opin. Biotechnol.* 14:177-193). Cytoskeleton and vesicle trafficking dynamics help to target plant defense responses asymmetrically within plant cells, toward the point of pathogen attack.

Plant immune systems can also respond to an initial infection in one part of the plant by physiologically elevating the capacity for a successful defense response in other parts of the plant. These responses include systemic acquired resistance, largely mediated by salicylic acid-dependent pathways, and induced systemic resistance, largely mediated by jasmonic acid-dependent pathways. Against viruses, plants often induce pathogen-specific gene silencing mechanisms mediated by RNA interference. These are primitive forms of adaptive immunity.

In a small number of cases, plant genes have been identified that are broadly effective against an entire pathogen species (against a microbial species that is pathogenic on other genotypes of that host species). Examples include barley MLO against powdery mildew, wheat Lr34 against leaf rust, and wheat Yr36 against stripe rust. An array of mechanisms for this type of resistance may exist depending on the particular gene and plant-pathogen combination. Other reasons for effective plant immunity can include a relatively complete lack of co-adaptation (the pathogen and/or plant lack multiple mechanisms needed for colonization and growth within that host species), or a particularly effective suite of pre-formed defenses.

Resistance to disease varies among plants. It may be either total (a plant is immune to a specific pathogen) or partial (a plant is tolerant to a pathogen, suffering minimal injury). The two broad categories of resistance to plant diseases are vertical (specific) and horizontal (nonspecific). A plant variety that exhibits a high degree of resistance to a single race, or strain, of a pathogen is said to be vertically resistant; this ability usually is controlled by one or a few plant genes. Horizontal resistance, on the other hand, protects plant varieties against several strains of a pathogen, although the protection is not as complete. Horizontal resistance is more common and involves at least several or many genes.

Several means of obtaining disease-resistant plants are commonly employed alone or in combination. These include, but are not limited to, introduction from an outside source, selection, and induced variation. All three may be used at different stages in a continuous process; for example, varieties free from injurious insects or plant diseases may be introduced for comparison with local varieties. The more promising lines or strains are then selected for further propagation, and they are further improved by promoting as much variation as possible through hybridization or special treatment. Finally, selection of the plants showing greatest promise takes place.

Methods used in breeding plants for disease resistance are similar to those used in breeding for other characters. It is necessary to know as much as possible about the nature of inheritance of the resistant characters in the host plant and the existence of physiological races or strains of the pathogen.

Plant Resistance To Viruses

There are about over 400 species of plant-pathogenic viruses, which cause a range of diseases (Fauquet et al., *Virus taxonomy: classification and nomenclature of viruses: eighth report of the International Committee on the Taxonomy of Viruses*, 2005, Published by Academic Press, ISBN 0122499514, 9780122499517, incorporated herein by reference in its entirety). Plant viruses can be divided into two groups depending on their genomes. In one group, viruses have genomes that are reverse transcribed during the expression of their genomes (retroid), and then encapsidate either an RNA copy (retroviruses) or a DNA copy (pararetroviruses) of the genomes; In the other group, viruses have genomes that are not reverse transcribed (nonretroid). The nonretroid viruses can be further divided according to the type of genome nucleic acid encapsidated in virus particles, e.g., ssDNA, dsRNA, negative/ambisense ssRNA, or positive/sense ssRNA.

Non-limiting examples of plant viruses include, ssDNA genomes viruses (e.g., family Geminiviridae), reverse transcribing viruses (e.g., families Caulimoviridae, Pseudoviridae, and Metaviridae), dsNRA viruses (e.g., families Reoviridae and Partitiviridae), (−) ssRNA viruses (e.g., families Rhabdoviridae and Bunyaviridae), (+) ssRNA viruses (e.g., families Bromoviridae, Closteroviridae, Comoviridae, Luteoviridae, Potyviridae, Sequiviridae and Tombusviridae) and viroids (e.g., families Pospiviroldae and Avsunviroidae). Detailed classification information of plant viruses can be found in Fauquet et al., supra.

The interactions between plants and viruses are complex. The best characterized mechanism of plant antiviral defense is mediated by resistance (R) genes. R genes confer resistance to organisms including viruses, bacteria, fungi and nematodes (Martin et al., Understanding the functions of plant disease resistance proteins. 2003, *Annu. Rev. Plant Biol.* 54:23-61). Another mechanism of plant antiviral defense is mediated by RNA-silencing pathways.

Most R-gene-mediated resistance responses lead to hypersensitive response (HR). The HR includes programmed cell death (PCD), which occurs in cells at the site of infection and manifests as discrete necrotic lesions in otherwise phenotypically normal tissue. The virus is usually confined to the lesion and to the cells immediately surrounding it and fails to spread from lesions into adjacent healthy tissues. R-gene mediated resistance also sometime leads to systemic acquired resistance (SAR), which occurs in tissues that are distant from the initial infection site and renders them immune to infection by the same or closely related pathogens. SAR can last for several weeks, characterized by the increased expression of several genes, named pathogenesis-related genes, that encode antimicrobial compounds. Several R genes responsible for resistant to plant viruses have been isolated using methods known to those skilled in the art.

Proteins encoded by R genes all belong to the NB-ARC-LRR superfamily (NB-ARC-LRR refers to nucleotide-binding domain—Apaf-1 and CED4 similar domain—Leicome-rich repeats). This superfamily highly resembles the mammalian NODS (nucleotide-binding oligomerization domain) proteins, which are intracellular NB-ARC-LRR proteins involved in defense (see Inohara et al., NODs: intracellular proteins involved in inflammation and apoptosis. 2003, *Nature Rev. Immunol.* 3:371-382). Two subgroups of NB-ARC-LRR proteins are Tol-linter-leukin-1 receptor domain (TIR)-NB-ARC-LRR proteins and coiled-coil domain (CC)-NB-ARC-LRR proteins. TIR, NB-ARC and LRR domains are also found in molecules that are important for animal innate immunity. It is generally recognized that the TIR domain and CC domain of R proteins have roles in confirming recognition specificity of R proteins.

R genes in plants are tightly regulated in plants under normal conditions, since abnormal activation in absence of virus effectors may lead to plant cell deaths. Such regulation can be transcriptional (Jordan et al., Alternative splicing of transcripts encoding Toll-like plant resistance proteins—what's the functional relevance to innate immunity? 2002, *Trends Plant Sci.* 7:392-398), translational (Bhattacharjee et al., Virus resistance induced by NB-LRR proteins involves Argonaute4-dependent translational control, *The Plant Journal*, 58:940-951, 2009), or post-translational (Mackey et al., Arabidopsis RIN4 is a target of the type III virulence effector AvrRpt2 and modulates RPS2-mediated resistance. *Cell* 112: 379-389 (2003); Axtell et al., Initiation of RPS2-specified disease resistance in Arabidopsis is coupled to the AvrRpt2-directed elimination of RIN4. *Cell* 112:369-377 (2003); and Shao et al., Cleavage of Arabidopsis PBS1 by a bacterial type III effector. *Science* 301:1230-1233 (2003)).

Viral protein can function as an avirulent factor that is specifically recognized by a given R protein. Without wishing to be bound by theory, the recognition can be a simple receptor-ligand recognition (e.g., Martin et al., Understanding the functions of plant disease resistance proteins. *Annu. Rev. Plant Biol.* 54, 23-61 (2003)), or a more sophisticated mechanism as known as the 'guard hypothesis" (e.g., Van der Biezen & Jones Plant disease resistance proteins and the gene-for-gene concept. *Trends Biochem. Sci.* 23, 454-456 (1998)). HRT (an R protein)-TCV coat protein (a viral protein) induced plant resistance to TCV is a good example of guard hypothesis (Ren et al., HRT gene function requires interaction between a NAC protein and viral capsid protein to confer resistance to turnip crinkle virus. *Plant Cell* 12:1917-1926 (2000)).

Recognition between an R protein and a viral protein can lead to activation of downstream signaling pathways (e.g., kinase cascades), alteration of transcriptional profiles, generation of reactive oxygen species (ROS), and production of nitric oxide (NO). In addition, plant hormones signaling are involved. Often as a result, hypersensitive reaction happens and consequential programmed plant cell death restricts the spreading of virus. Following the HR, a secondary defense response, systemic acquired resistance (SAR), is activated and the plant gains long-lasting resistance to the virus.

Geminivirus

Geminiviruses are plant viruses that belong to the family Geminiviridae, first described by Goodman in 1977. Geminiviruses are characterized by the unique twin shape of a fused icosahedral viral particle. Geminiviruses are plant viruses which have ambisense single-stranded circular DNA genomes and are members of class II of the Baltimore classification of viruses. The genome can either be a single component of 2500-3000 nucleotides, or two similar-sized components. They have an elongated, geminate capsid with two incomplete T=1 icosahedra joined at the missing vertex. The capsids range from 18-20 nm in diameter with a length of about 30 nm. Viruses with bipartite genomes (begomoviruses only) have these components separated into two different particles, therefore more than one virus particle is required to infect a cell. Transmission of these viruses can be via leafhoppers (mastreviruses, curtoviruses) or via one species of whitefly (begomoviruses) or via treehoppers (topocuviruses).

These viruses are responsible for a significant amount of crop damage worldwide. Diseases caused by geminiviruses have long been recognized as a limitation to the cultivation of several important crops, including maize, cassava, bean, squash, cucurbits, and tomato, et al. Epidemics of geminivirus diseases have arisen due to a number of factors, including the recombination of different geminiviruses co-infecting a plant, which enables novel, possibly virulent viruses to be developed. Other contributing factors include the transport of infected plant material to new locations, expansion of agriculture into new growing areas, and the expansion and migration of vectors that can spread the virus from one plant to another.

Geminiviruses comprise a large and diverse family of viruses that infect a wide range of important monocotyledonous and dicotyledonous crop species and cause significant yield losses. Geminiviruses are classified into four genera: genus Mastrevirus (e.g., Maize streak virus), genus Curtovirus (e.g., Beet curly top virus), genus Begomovirus (e.g., SLCV), and genus Topocuvirus (Tomato pseudo-curly top virus).

The genus Begomovirus contains more than 200 viral species (Fauquet et al., 2008, "Geminivirus strain demarcation and nomenclature". *Archives of Virology* 153:783-821, incorporated herein by reference in its entirety), and belong to the taxonomic family Geminiviridae. They are plant viruses that as a group have a very wide host range. Natural hosts of begomoviruses are plant species in which the virus can replicate, cause systemic infection, and encapsidate, and from which virions are ingested and transmitted to a susceptible host by the whitefly vector (Funayama, "Effects of Virus Infection and Light Environment on Population Dynamics of Eupatorium makinoi (Asteraceae)", 2001, *American Journal of Botany* 88: 616). Worldwide they are responsible for a large amount of economic damage to many important agronomic and horticultural crops such as tomatoes, beans, squash, cassava and cotton in subtropical and tropical regions of Americas, Africa and Asia. Morphologically, Begomovirus particles are non-enveloped. The nucleocapsid is 38 nm long and 15-22 nm in diameter. While particles have basic isocaherdal symmetry, they consist of two incomplete icosahedra—missing one vertex—joined together. There are 22 capsomeres per nucleocapsid. Begomovirus species has single stranded closed circular DNA. Most begomoviruses have a bipartite genome, meaning that the genome is segmented into two segments (referred to as DNA A and DNA B) that are packaged into separate particles. Both segments are generally required for successful symptomatic infection in a host cell, but DNA B is dependent for its replication upon DNA A, which can in some begomoviruses apparently cause infections on its own.

Squash Leaf Curl Virus (SLCV)

Squash Leaf Curl Virus, also as known as the Squash Leaf Curl Bigeminivirus, Melon Leaf Curl Virus (Duffus, Liu & Johns, *Phytopathology* 75: 1312, 1985), or Watermelon Curly Mottle Virus (Brown & Nelson, *Phytopathology* 74: 1136, 1984; Brown & Nelson, *Phytopathology* 76: 236, 1986), was insect-transmitted virus first described by Flock & Mayhew (Flock & Mayhew, *Pl. Dis.* 65: 75, 1981).

Squash leaf curl virus (SLCV) is a virus with geminate particles, 22×38 nm. The circular ssDNA genome is bipartite and consists of two similar-sized species. Known hosts are in the Cucurbitaceae, Leguminosae, Solanaceae and Euphorbiaceae. The virus is transmitted by the whitefly, Bemisia tabaci, especially biotype B, and by inoculation with sap. Squash leaf curl disease occurs in desert regions of southwestern USA (e.g., Arizona, California, and Texas), Mexico, Costa Rica, Dominican Republic, Guatemala, Honduras, Nicaragua and Middle East.

SLCV causes severe systemic stunting and leaf curl in cucurbits. SLCV causes severe losses of squashes, melons and related cucurbits worldwide. Symptoms of the disease are curled leaves with yellowed, mottled areas. Leaves have shortened petioles that cluster around the vines (Antignus et al., 2003; Idris et al., 2006). At least several strains of SLCV have been isolated before. Isolates of SLCV can be grouped into at least two strains based on host range:

1. SLCV-2 (Dodds et al., *Phytopathology* 74: 221, 1984) and MLCV (Duffus, Liu & Johns, *Phytopathology* 75: 1312, 1985) from the Imperial Valley, California, USA, and WMC-MoV (Brown & Nelson, *Phytopathology* 76: 236, 1986) from Arizona, USA are able to infect watermelon, melon, and cucumber. MLCV and WMCMoV were initially described as distinct viruses, but may be considered, along with SLCV-2, as isolates of a wide host range strain of SLCV. They are closely related to a fourth isolate (SLCV-E, Polston, Dodds & Perring, *Phytopathology* 79: 1123, 1989) for which infective DNA clones have been characterized and completely sequenced (Lazarowitz S G. (1991) Molecular characterization of two bipartite geminiviruses causing squash leaf curl disease: role of replication and movement functions determining host range. *Virology* 180:70-80; Lazarowitz & Lazdins, *Virology* 180: 58, 1991).

2. The SLCV isolate of Cohen et al. (Cohen, Duffus, Larsen, Liu & Flock, *Phytopathology* 73: 1669, 1983) has a narrow host range which does not include watermelon, melon or cucumber. An additional narrow host range isolate (SLCV-R) was cloned from a mixed culture also containing SLCV-E (Lazarowitz & Lazdins, 1991; Lazarowitz, 1991). Host range properties of SLCV-R are complex, with restriction in certain species being determined by variants of the DNA B component (Lazarowitz, 1991). Nucleic acid hybridization tests with component-specific probes (Polston, Dodds & Perring, *Phytopathology* 79: 1123, 1989) suggest that SLCV-R and the SLCV isolate of Cohen et al. (1983, supra) are isolates of the same strain.

The symptoms induced by SLCV in each host may vary. In winter squash, severe stunting and leaf curl symptoms occur on new growth. Interveinal tissue sometime become mottled, and green vein-banding may be associated with leaf veins. Enations often form on the lower surface of symptom-bearing leaves, and occasionally, flowers fail to develop or set fruit, or fruits may be small and distorted. Similar symptoms develop on infected summer squash and pumpkin (e.g., *C. pepo*). In *Phaseolus vulgaris*, for example, in Bean cultivars Tender Crop, Top Crop, Earliwax, Majestic and Greenpak develop a systemic green mosaic and veinal distortion, resulting in twisted, deformed leaves. In *Citrullus lanatus*(watermelon), *Cucumis melo* (melon), and *Cucumis sativa* (cucumber), the three old world cucurbit species, the wide host range isolates SLCV-2, MLCV and WMCMoV induce leaf curling and stunting symptoms, whereas the narrow host range SLCV does not.

Cucurbitaceae

Cucurbitaceae is a plant family commonly known as melons, gourds or cucurbits and includes crops like cucumbers, squashes (including pumpkins), luffas, melons and watermelons. The family is predominantly distributed around the tropics, where those with edible fruits were amongst the earliest cultivated plants in both the Old and New Worlds.

Cucurbits is a general term for the species of the Cucurbitaceae family, comprising about 140 genera and more that 900 species of which only a few are cultivated. The world production of cucurbit crops is in excess of 115 million metric tons, on a total area harvested of 6.9 million hectares throughout the world (FAPSTAT database, 2000). The world production and the harvested area has increased three-fold in the last three decades.

Most of the plants in this family are annual vines but there are also woody lianas, thorny shrubs, and trees (Dendrosicyos). Many species have large, yellow or white flowers. The stems are hairy and pentangular. Tendrils are present at 90° to the leaf petioles at nodes. Leaves are exstipulate alternate simple palmately lobed or palmately compound. The flowers are unisexual, with male and female flowers on different plants (dioecious) or on the same plant (monoecious). The female flowers have inferior ovaries. The fruit is often a kind of berry called a pepo.

There are about more than 140 extant genera in Cucurbitaceae, including over 900 species. Cucurbitaceae includes subfamily Zanonioideae and subfamily cucurbitoideae.

Subfamily Zanonioideae includes subtribe Fevilleinae (e.g., *Fevillea*), subtribe Zanoniinae (e.g., *Alsomitra, Zanonia, Siolmatra, Gerrardanthus, Zygosicyos, Xerosicyos, Neoalsomitra*), subtribe Gomphogyninae (e.g., *Hemsleya, Gomphogyne, Gynostemma*), subtribe Actinostemmatinae (e.g., *Bolbostemma, Actinostemma*), and subtribe Sicydiinae (e.g., *Sicydium Chalema Pteropepon Pseudosicydium Cyclantheropsis*).

Subfamily Cucurbitoideae includes subtribe Dendrosicyinae (e.g., *Kedrostis, Dendrosicyos, Corallocarpus, Ibervillea, Tumamoca, Halosicyos, Ceratosanthes, Doyerea, Trochomeriopsis, Seyrigia, Dieterlea, Cucurbitella, Apodanthera, Guraniopsis, Melothrianthus, Wilbrandia*), subtribe Guraniinae (e.g., *Helmontia, Psiguria, Gurania*), subtribe Cucumerinae (e.g., *Melancium, Cucumeropsis, Posadaea, Melothria, Muellarargia, Zehneria*, Cucumis (including: *Mukia, Dicaelospermum, Cucumella, Oreosyce*, and *Myrmecosicyos*)), subtribe Trochomeriinae (e.g., *Solena, Trochomeria, Dactyliandra, Ctenolepsis*), tribe Schizopeponeae (e.g., *Schizopepon*), subtribe Thladianthinae (e.g., *Indofevillea, Siraitia, Thladiantha, Momordica*), subtribe Telfairiinae (*Telfaria*), subtribe Hodgsoniinae (*Hodgsonia*), subtribe Ampelosicyinae (e.g., *Ampelosicyos, Peponium*), subtribe Trichosanthinae (e.g., *Gymnopetalum, Trichosanthes, Tricyclandrai*), subtribe Herpetosperminae (e.g., *Cephalopentandra, Biswarea, Herpetospermum, Edgaria*), subtribe Benincasinae (e.g., *Cogniauxia, Ruthalicia, Lagenaria, Benincasa, Praecitrullus, Citrullus, Acanthosicyos, Eureiandra, Bambekea, Nothoalsomitra, Coccinia, Diplocyclos, Raphidiocystis, Lemurosicyos, Zombitsia, Ecballium, Bryonia*), subtribe Luffinae (*Luffa*), tribe Cucurbiteae (e.g., *Cucurbita, Sicana, Tecunumania, Calycophysum, Peponopsis, Anacaona, Polyclathra, Schizocarpum, Penelopeia, Cionosicyos, Cayaponia, Selysia, Abobra*), subtribe cyclantherinae (e.g., *Hanburia, Echinopepon, Marah, Echinocystis, Vaseyanthus, Brandegea, Apatzingania, Cremastopus, Elateriopsis, Pseudocyclanthera, Cyclanthera, Rytidostylis*), and subtribe Sicyinae (e.g., *Sicyos, Sicyosperma, Parasicyos, Microsechium, Sechium, Sechiopsis, Pterosicyos*).

Cucurbita

*Cucurbita* is a genus in the gourd family Cucurbitaceae first cultivated in the Americas and now used in many parts of the world (Whitaker, 1947, "American origin of cultivated cucurbits". *Annals of the Missouri Botanical Garden* 34: 101-111; Whitaker, 1956, "The origin of the cultivated cucurbita". The American Naturalist 90 (852): 171-176). It includes species grown for their fruit and edible seeds (the squashes, pumpkins marrows, and the chilacayote), as well as some species grown only as gourds. These gourds (and other squashes) come in many colors, including blue, orange, yellow, red, and green. They have bicollateral vascular bundles. Many North and Central American species are visited by specialist pollinators in the apid group Eucerini, especially the genera Peponapis and Xenoglossa, and these bees can be very important for fruit set. Non-limiting examples of *Cucurbita* species include, *C. argyrosperma/C. mixta*—cushaw; *C. digitata*—fingerleaf gourd; *C. ficifolia*—figleaf gourd, chilacayote; *C. foetidissima*—stinking gourd, buffalo gourd; *C. maxima*—winter squash, pumpkin; *C. moschata*—butternut squash, "dickinson" pumpkin; *C. okeechobeensis; C. palmata; C. pepo*—acorn squash, field pumpkin; yellow summer squash; zucchini; small multicolored gourds and many others.

Squash

Squash is the common name for a collection of plants that produce edible seeds, fruits and flowers. Squashes generally refer to four species of the genus *Cucurbita* native to Mexico and Central America, also called marrows depending on variety or the nationality of the speaker. These species include *C. maxima* (e.g., hubbard squash, buttercup squash), *C. mixta* (a.k.a. *C. argyrosperma*, e.g., cushaw squash), *C. moschata* (e.g., butternut squash), and *C. pepo*(most pumpkins, acorn squash, summer squash, zucchini). It is also natively grown in other parts of North America, and in Europe, India, and Australia. In North America, squash is loosely grouped into summer squash or winter squash, as well as autumn squash (another name is cheese squash) depending on whether they are harvested as immature vegetables (summer squash) or mature vegetables (autumn squash or winter squash). Gourds are from the same family as squashes. Well known types of squash include the pumpkin and zucchini. Giant squashes are derived from *Cucurbita maxima* and are routinely grown to weights nearing those of giant pumpkins. Non-limiting examples of squash species include, *C. maxima* (e.g., winter squash, ambercup squash, autumn cup squash, banana squash, buttercup squash, kabocha squash, hubbard squash, and turban squash), *C. mixta* (a.k.a. *C. argyrosperma*, e.g., cushaw squash), *C. moschata* (winter crookneck squash, e.g., butternut squash), *C. pepo* var. *pepo* (most pumpkins, acorn squash), and *C. pepo* var. *melopepo* (e.g., summer squash (bush summer squash zucchini)), carnival squash, delicata squash, gold nugget squash, spaghetti squash, and sweet dumpling squash.

Winter squashes are the mature fruits of three Cucurbit species: *Cucurbita maxima, Cucurbita moschata* and *Cucurbita pepo*. Fruit from winter squash varieties are grown to physiological maturity and typically stored for consumption during the winter months or used for ornamental purposes. Examples of common winter squashes are acorn, butternut, hubbard, and spaghetti squash, as well as the Halloween type pumpkins. *Cucurbita maxima* is one of the most diverse domesticated species, perhaps with more cultivated forms than any other crop. This species originated in South America from the wild *C. maxima* ssp. andreana over 4000 years ago. Different squash types of this species were introduced into North America as early as the 16th century. By the early 19th century, at least three varieties are known to have been commercially introduced in North America from seeds obtained from Native Americans. Secondary centers of diversity include India, Bangladesh, Burma, and possibly the southern Appalachians. Non-limiting examples of *Cucurbita maxima* include, Banana squash, Buttercup squash, Jarrandale pumpkin, Kabocha, Lakota squash, Arikara squash, and Hubbard squash. Candyroaster landrace *Cucurbita moschata* is a species that includes some varieties of squash and pumpkin. *C. moschata* squash are generally more tolerant of hot, humid weather than *C. maxima* or *C. pepo*. They also generally display a greater resistance to disease and insects, especially to the squash vine borer. Non-limiting examples of *C. moschata* include, butternut squash, Dickinson field pumpkin, Kentucky field pumpkin, Long Island cheese pumpkin, Calabaza pumpkin, Seminole pumpkin, Neck pumpkin, and Long of Naples squash. *Cucurbita pepo* is the main economic squash species. It includes varieties of squash, gourd, and pumpkin. Non-limiting example of *Cucurbita pepo* include, Acorn squash, Delicata squash, Gem squash, Heart of gold squash, Pattypan squash, Some types of Pumpkin, Spaghetti squash, Sweet dumpling squash, Yellow crookneck squash, Yellow summer squash, and Zucchini.

Most summer squash varieties are *Cucurbita pepo*, and their fruits are typically harvested and consumed at an immature stage. The flowers of summer squash can also be harvested for consumption. There are many types of summer squash, including yellow crookneck, yellow straightneck, scallop, Lebanese, and green and gray zucchini. Green zucchini is the type of *C. pepo* squash preferred by consumers in Europe and many parts of the North America, as well as in other regions. Unlike winter squashes, summer squash fruit have a short shelf life, and are typically consumed within days of harvest. Because of the extended ability to ship produce over long distances there are some markets where the teens "summer" and "winter" squash no longer reflect a restriction on availability and all types can be found in these markets year round.

Novel Resistance to SLCV in Cucurbits

The inventors of the present invention separately discovered two different groups of *C. moschata* that displayed SLCV resistant: the first group was designated as 'WSXP1030'; the second group consisted of five lines designated as 'CT1' to 'CT5'. As demonstrated in the Example section, our analysis indicates that 'WSXP1030', 'CT3' and 'CT4' are the lines having the most interesting resistance levels, and at least the resistance to SLCV in 'WSXP1030' and 'CT4' is due to the same genetic locus, herein newly designated as the slc-2 gene.

Cucurbit seeds comprising the slc-2 gene were deposited as NCIMB Accession No. 41728. The seeds come from the inbred cucurbit plant designated as N9N030. Accordingly, the present invention provides cucurbit seeds containing a single recessive SLCV resistance gene slc-2, wherein the SLCV resistant gene slc-2 is present in the cucurbit seeds deposited as NCIMB Accession No. 41728. The cucurbit seeds of the present invention can be used to produce cucurbit plants resistant to SLCV. In one embodiment, said cucurbit plants are any non-*C. moschata* cucurbit plants. In one embodiment, said cucurbit plants are produced by growing said cucurbit seeds containing the single recessive gene slc-2. In other embodiments, new cucurbit plants can be derived from a cross wherein at least one parent comprises the recessive gene slc-2 as described above, using breeding methods described elsewhere herein. The parent comprising the recessive gene slc-2 can be either resistant to SLCV, or susceptible to SLCV (e.g., due to heterologous alleles). In one embodiment, the presence of the recessive slc-2 gene in the cucurbit plant is characterized by at least one molecular marker which defining primers are in Table 8. One skilled in the art would be able to design other primers for PCR detection of the molecular markers defined by the primers listed in Table 8, or methods other than PCR to detect said molecular markers (e.g., polymorphism detection methods such as nucleic acid sequencing and TILING arrays). Additional breeding methods have been known to one of ordinary skill in the art, e.g., methods discussed in Chahal and Gosal (Principles and procedures of plant breeding: biotechnological and conventional approaches, CRC Press, 2002, ISBN 084931321X, 9780849313219), Taji et al. (In vitro plant breeding, Routledge, 2002, ISBN 156022908X, 9781560229087), Richards (Plant breeding systems, Taylor & Francis US, 1997, ISBN 0412574500, 9780412574504), Hayes (Methods of Plant Breeding, READ BOOKS, 2007, ISBN 1406737062, 9781406737066), and Lörz et al. (Molecular marker systems in plant breeding and crop improvement, Springer, 2005, ISBN 3540206892, 9783540206897), each of which is incorporated by reference in its entirety.

The present invention also provides a seed, a fruit, a plant population, a plant, a plant part, a plant cell and/or a plant tissue culture derived from the plants comprising the recessive gene slc-2 as described above. In one embodiment, the invention provides an embryo, a pollen and/or an ovule of the plants comprising the recessive gene slc-2. The present invention also provides a tissue culture of the regenerable cells of the plants comprising the recessive gene slc-2, plant parts, plant tissue or plant cells, wherein said tissue culture retains the recessive gene slc-2. In one embodiment, the regenerable cells are derived from embryos, protoplasts, meristematic cells, callus, pollen, leaves, anthers, stems, petioles, roots, root tips, fruits, seeds, flowers, cotyledons, or hypocotyls.

Modern plant tissue culture is performed under aseptic conditions under filtered air. Living plant materials from the environment are naturally contaminated on their surfaces (and sometimes interiors) with microorganisms, so surface sterilization of starting materials (explants) in chemical solutions (usually alcohol or bleach) is required. Explants are then usually placed on the surface of a solid culture medium, but are sometimes placed directly into a liquid medium, particularly when cell suspension cultures are desired. Solid and liquid media are generally composed of inorganic salts plus a few organic nutrients, vitamins and plant hormones. Solid media are prepared from liquid media with the addition of a gelling agent, usually purified agar.

The composition of the medium, particularly the plant hormones and the nitrogen source (nitrate versus ammonium salts or amino acids) have profound effects on the morphology of the tissues that grow from the initial explant. For example, an excess of auxin will often result in a proliferation of roots, while an excess of cytokinin may yield shoots. A balance of both auxin and cytokinin will often produce an unorganized growth of cells, or callus, but the morphology of the outgrowth will depend on the plant species as well as the medium composition. As cultures grow, pieces are typically sliced off and transferred to new media (subcultured) to allow for growth or to alter the morphology of the culture. The skill and experience of the tissue culturist are important in judging which pieces to culture and which to discard. As shoots emerge from a culture, they may be sliced off and rooted with auxin to produce plantlets which, when mature, can be transferred to potting soil for further growth in the greenhouse as normal plants.

The tissue obtained from the plant to culture is called an explant. Based on work with certain model systems, particularly tobacco, it has often been claimed that a totipotent explant can be grown from any part of the plant. However, this concept has been vitiated in practice. In many species explants of various organs vary in their rates of growth and regeneration, while some do not grow at all. The choice of explant material also determines if the plantlets developed via tissue culture are haploid or diploid. Also the risk of microbial contamination is increased with inappropriate explants. Thus it is very important that an appropriate choice of explant be made prior to tissue culture.

The specific differences in the regeneration potential of different organs and explants have various explanations. The significant factors include differences in the stage of the cells in the cell cycle, the availability of or ability to transport endogenous growth regulators, and the metabolic capabilities of the cells. The most commonly used tissue explants are the meristematic ends of the plants like the stem tip, auxiliary bud tip and root tip. These tissues have high rates of cell division and either concentrate or produce required growth regulating substances including auxins and cytokinins. Some explants, like the root tip, are hard to isolate and are contaminated with soil microflora that become problematic during the tissue culture process. Certain soil microflora can form tight associations with the root systems, or even grow within the root. Soil particles bound to roots are difficult to remove without injury to the roots that then allows microbial attack. These associated microflora will generally overgrow the tissue culture medium before there is significant growth of plant tissue. Aerial (above soil) explants are also rich in undesirable microflora. However, they are more easily removed from the explant by gentle rinsing, and the remainder usually can be killed by surface sterilization. Most of the surface microflora do not form tight associations with the plant tissue. Such associations can usually be found by visual inspection as a mosaic, de-colorization or localized necrosis on the surface of the explant.

An alternative for obtaining uncontaminated explants is to take explants from seedlings which are aseptically grown from surface-sterilized seeds. The hard surface of the seed is less permeable to penetration of harsh surface sterilizing agents, such as hypochlorite, so the acceptable conditions of sterilization used for seeds can be much more stringent than for vegetative tissues.

Tissue cultured plants are clones, if the original mother plant used to produce the first explants is susceptible to a pathogen or environmental condition, the entire crop would be susceptible to the same problem, conversely any positive traits would remain within the line also. Plant tissue culture is used widely in plant science; it also has a number of commercial applications. Applications include:

1. Micropropagation is widely used in forestry and in floriculture. Micropropagation can also be used to conserve rare or endangered plant species.
2. A plant breeder may use tissue culture to screen cells rather than plants for advantageous characters, e.g. pathogen resistance/tolerance.
3. Large-scale growth of plant cells in liquid culture inside bioreactors as a source of secondary products, like recombinant proteins used as biopharmaceuticals.
4. To cross distantly related species by protoplast fusion and regeneration of the novel hybrid.
5. To cross-pollinate distantly related species and then tissue culture the resulting embryo which would otherwise normally die (Embryo Rescue).
6. For production of doubled monoploid (dihaploid) plants from haploid cultures to achieve homozygous lines more rapidly in breeding programs, usually by treatment with colchicine which causes doubling of the chromosome number.
7. As a tissue for transformation, followed by either short-term testing of genetic constructs or regeneration of transgenic plants.
8. Certain techniques such as meristem tip culture can be used to produce clean plant material from virused stock, such as potatoes and many species of soft fruit.
9. Micropropagation using meristem and shoot culture to produce large numbers of identical individuals.

Exemplary tissue culture methods for cucurbit plants have been described by Fadia et al. (Tissue culture studies on cucurbits: the effect of NAA, sucrose and kinetin on tracheal differentiation in Cucumis tissues cultured in vitro, *Phytomorphology*, Vol 26), and Trigiano et al (Plant Tissue Culture Concepts and Laboratory Exercises, Publisher CRC Press, 2000 ISBN 0849320291, 9780849320293).

The present invention also provides a cutting, a rootstock, a scion, or an explant from the SLCV resistant plants as described above for grafting.

Grafting is a method of asexual plant propagation widely used in agriculture and horticulture where the tissues of one plant are encouraged to fuse with those of another. It is most commonly used for the propagation of trees and shrubs grown commercially. In most cases, one plant is selected for its roots, and this is called the stock or rootstock. The other plant is selected for its stems, leaves, flowers, or fruits and is called the scion. The scion contains the desired genes to be duplicated in future production by the stock/scion plant. In stem grafting, a common grafting method, a shoot of a selected, desired plant cultivar is grafted onto the stock of another type. In another common form called budding, a dormant side bud is grafted on the stem of another stock plant, and when it has fused successfully, it is encouraged to grow by cutting out the stem above the new bud.

For successful grafting to take place, the vascular cambium tissues of the stock and scion plants must be placed in contact with each other. Both tissues must be kept alive until the graft has taken, usually a period of a few weeks. Successful grafting only requires that a vascular connection takes place between the two tissues. A physical weak point often still occurs at the graft, because the structural tissue of the two distinct plants, such as wood, may not fuse.

Exemplary grafting techniques include, approach grafting, budding grafting (patch budding, chip budding, T-budding), cleft grafting, side grafting, whip grafting, stub grafting, awl grafting, veneer grafting, bark grafting, tongue grafting, et al. A detailed grafting method for cucurbits is described by Davis et al. (Cucurbit Grafting, *Critical Reviews in Plant Sciences*, January 2008, 27(1): 50-74).

The present invention also provides a progeny derived from the SLCV resistant plant as described above, whether produced sexually or asexually, wherein said progeny retains resistance to SLCV. In one embodiment, at least 5% of said progeny is resistant to SLCV. For example, about 5% to about 15%, about 16% to about 25%, about 26% to about 50%, or 51% to about 99%, or more of said progeny is resistant to SLCV.

The SLCV resistant plants of the present invention can be used for many purposes. In one embodiment, a SLCV resistant plant is used as a donor plant of genetic material which can be transferred to a recipient plant to produce a plant which has the transferred genetic material and is also resistant to SLCV. Any suitable method known in the art can be applied to transfer genetic material from a donor plant to a recipient plant. In most cases, such genetic material is genomic material.

In one embodiment, the whole genome of the SLCV resistant plants of the present invention is transferred into a recipient plant. This can be done by crossing the SLCV resistant plants to a recipient plant to create a F1 plant. The F1 plant can be further selfed and selected for one, two, three, four, or more generations to give SLCV resistant plants.

In another embodiment, at least the resistance-conferring parts of the donor plant's genome are transferred. This can be done by crossing the SLCV resistant plants to a recipient plant to create a F1 plant, followed with one or more backcrosses to one of the parent plants to give SLCV resistant plants with the desired genetic background. The progeny resulting from the backcrosses can be further selfed to give SLCV resistant plants.

According to the analysis on a segregation population of 28 F2 plants, the nature of the novel resistance to SLCV of the present invention is a single recessive locus. Without wishing to be bound by a particular theory, the resistance conferring part is believed to be a single recessive gene designated as slc-2 in the genome. Thus, in another embodiment, the minimum genome segment comprising the slc-2 gene can be transferred to a recipient line through breeding methods. As also described elsewhere herein, molecular marker assisted selection can be used to facilitate the breeding.

In some embodiments, the recipient plant is a squash plant, or any other cucurbit plants that can hybridize with the SLCV resistant plants of the present invention.

and Bemis (Meiotic Irregularities in *Cucurbita* Species Hybrids, May 1967; 58: 109-111); Bemis (Triple haploids in *Cucurbita*, March 1973; 64: 103-104; and Grubben (Vegetables, Vol. 2 of Plant resources of tropical Africa), each of which is incorporated by reference in its entirety.

Some cucurbit species hybridize with other cucurbit species, as shown Table 1 below.

TABLE 1

Ability of cucurbit species to cross.

| Crop | Cuke | Melon | Wtr | Sqsh | Pmp | G-Cu | G-Wx | G-Lg | G-Lf | G-Rg |
|------|------|-------|-----|------|-----|------|------|------|------|------|
| Cuke | X | — | — | — | — | — | — | — | — | — |
| Melon | — | X | — | — | — | — | — | — | — | — |
| Wtr | — | — | X | — | — | — | — | — | — | — |
| Sqsh | — | — | — | X | X | X | — | — | — | — |
| Pmp | — | — | — | X | X | X | — | — | — | — |
| G-Cu | — | — | — | X | X | X | — | — | — | — |
| G-Wx | — | — | — | — | — | — | X | — | — | — |
| G-Lg | — | — | — | — | — | — | — | X | — | — |
| G-Lf | — | — | — | — | — | — | — | — | X | — |
| G-Rg | — | — | — | — | — | — | — | — | — | X |

X = will cross
— = will not cross
Cuke = cucumber (*Cucumis sativus*)
Melon = melon (*Cucumis melo*)
Wtr = watermelon (*Citrullus lanatus*) and citron (*C. lanatus* var. *citroides*)
Sqsh = squash (*Cucurbita pepo, C. maxima, C. moschata, C. argyrosperma*)
Pmp = pumpkin (*Cucurbita pepo, C. maxima, C. moschata, C. argyrosperma*)
G-Cu = gourd-*cucurbita* (*Cucurbita pepo, C. maxima, C. moschata, C. argyrosperma*)
G-Wx = gourd-wax (*Benincasa hispida*)
G-Lg = gourd-*lagenaria* (*Lagenaria siceraria*)
G-Lf = gourd-*luffa* (*Luffa aegyptiaca, L. cylindrica*)
G-Rg = gourd-ridge (*Luffa acutangula*)
Note:
Data is published by the Cucurbit Genetics Cooperative in North Carolina State University.

There has been much interest in hybridizing the cultivated species of *Cucurbita*. As a result, the relationship between the cultivated species has been studied extensively. All species in *Cucurbita* have the same chromosome number (2n=40). The interspecific cross of *C. moschata* with *C. maxima* and *C. argyrosperma* results in a viable F1 but sterile progeny; with *C. pepo* in sparingly fertile F1 plants, the F2 plants being sterile; with *C. ficifolia* in fruits without seed. A Japanese company developed a commercial interspecific F1 hybrid with *C. maxima* and *C. moschata* lines as parents. No spontaneous hybridization between the five cultivated *Cucurbit* species (*C. ficifolia, C. maxima, C. argyrosperma, C. moschata* and *C. pepo*) has been reported before. Results of interspecific hybridization suggest that the sterility barriers are genetic rather than the result of a lack of chromosomal homology, which means that heterozygosity improves the chances of obtaining interspecific hybrids. Hybridization between wild *Cucurbita* species and cultivated species have also been studied. *C. lundelliana*, a wild species, has been studied as it has received considerable attention as to its cross-compatibility with the cultivated species. For example, *C. lundelliana* can cross to *C. moschata, C. maxima*. Other non-limiting exemplary hybridizations include, cross between *C. andreana* and *C. maxima*, and between *C. moschata* and *C. foetidissima*. For more information of *Cucurbita* species hybridization, see Bemis and Nelson et al. (Interspecific Hybridization within the Genus *Cucurbita* I, Fruit Set, Seed and Embryo Development, 1963, Arizona-Nevada Academy of Science); Bemis et al (Interspecific hybridization in *Cucurbita*: II *C. moschata* Poir×Xerophytic Species of *Cucurbita*, November 1963; 54: 285-289); Groff In one embodiment, the recipient plant is an elite line having one or more certain agronomically important traits. As used herein, "agronomically important traits" include any phenotype in a plant or plant part that is useful or advantageous for human use. Examples of agronomically important traits include but are not limited to those that result in increased biomass production, production of specific biofuels, increased food production, improved food quality, etc. Additional examples of agronomically important traits includes pest resistance, vigor, development time (time to harvest), enhanced nutrient content, novel growth patterns, flavors or colors, salt, heat, drought and cold tolerance, and the like. Agronomically important traits do not include selectable marker genes (e.g., genes encoding herbicide or antibiotic resistance used only to facilitate detection or selection of transformed cells), hormone biosynthesis genes leading to the production of a plant hormone (e.g., auxins, gibberilins, cytokinins, abscisic acid and ethylene that are used only for selection), or reporter genes (e.g. luciferase, β-glucuronidase, chloramphenicol acetyl transferase (CAT, etc.).

Other agronomically important traits include resistance to biotic and/or abiotic stresses. As used herein, the phrase "biotic stress" or "biotic pressure" refers to a situation where damage is done to plants by other living organisms, such as bacteria, viruses, fungi, parasites, insects, weeds, animals and human. As used herein, the phrase "abiotic stress" or "abiotic pressure" refers to the negative impact of non-living factors on plants in a specific environment. The non-living variable must influence the environment beyond its normal range of variation to adversely affect the population performance or individual physiology of plants in a significant way. Non-limiting examples of stressors are high winds, extreme temperatures, drought, flood, and other natural disasters, such as tornados and wildfires. For example, the plant lines developed using the genetic materials and methods of the present invention can also include resistance to SLCV due to one or more different loci other than slc-2; resistance to other types of geminiviruses other than SLCV; and/or resistance to other pathogens (e.g., fungal plant pathogens, oomycetes, bacterial plant pathogens, insects et al.).

A list of popular North America squash cultivars with various agronomically important traits can be found in the Cucurbit Breeding database of North Carolina State University (Wessel-Beaver et al., Vegetable Cultivar Descriptions for North America, Squash, Retrieved on Apr. 21, 2010, incorporated by reference in its entirety).

In one embodiment, the recipient lines are resistant to SLCV due to one or more different loci other than slc-2, for example, the recipient lines are selected from the group consisting of:

'Depredator' from Seminis

'Shorouq' from S&G Vegetables (a company under Syngenta), white bulbous for Iran, asserted to be SLCV resistant.

'Rogers® Topazio' from Syngenta, grey type for Mexico, asserted to be SLCV resistant.

'Rogers® Cuarzo' from Syngenta, grey type for Mexico, asserted to be SLCV resistant.

'Jasper' (HZS-03-851) and Obsidian (HZS-03-847), from Dp Seeds, hybrid summer squash zucchinis asserted to be SLCV resistant.

'Greybeard' (HZS-03-853), from Dp Seeds, grey type, asserted to be SLCV resistant.

Sergio Garza's inbreds. Sergio Garza of the Universidad de Sonora in Hermosillo, Mexico (USON) developed an original donor source of intermediate resistance to geminivirus (including SLCV). The creation of this donor source began with the observation of a local Mexican landrace of *C. moschata* with resistance to geminivirus infection. Through many years of breeding, Mr. Garza developed an open pollinated variety of gray zucchini (*C. pepo*) with intermediate resistance to geminivirus infection. In 1998 USON made this variety available to seed companies with the goal of speeding the introduction of this resistance that would be valuable for local farmers. These lines include, USON line 211, USON line 212, USON line 214, USON line 215, USON line 232, USON line 253, USON line 262, and USON line 264.

The recipient line will have one or more preferred cucurbit traits. These traits include, but are not limited to, resistance/tolerance to pathogens, such as to Alternaria leaf spot (*Alternaria Cucumerina*), Angularlsp spot (*Pseudomonas syringae*), *Colletotrichum orbiculare, Edwinia tracheiphila*, Bean Yellow Mosaic Virus, Cucumber Mosaic Virus, downy mildew (*Pseudoperonospora cubensis*), fruit rot (*Rhizoctonia solani*), Fusarium wilt (*Fusarium solani f. cucurbitae*), gummy stem blight, melon mosaic virus, *phyllosticta cucurbitacearum*, phytophthora (*phytophthora capsici*), powdery mildew (*Erysiphe cichoracearum*), potyviruses (e.g., malva vein clearing potyvirus, potato virus Y, turnip mosaic virus, plum Pox Potyvirus, tulip breaking virus, papaya ringspot virus, apium virus Y, bidens mottle virus, celery mosaic virus, commelina mosaic virus, and tradescantia mosaic virus), seedling blight (*Pythum aphanidermatum, Pythum irregulare, Pythum ultimum, Rhizoctonia solani*), septoria (*Septoria cucurbitacearum*), stemphylium (*Stemphylium cucurbitacearum*), target leaf spot (*Corynespora cassiicola*), tobacco ringspot virus, and tomato ringspot virus; resistance/tolerance to insects such as to Atlantic spider mite, banded cucumber beetle, brown wheat mite, darkling ground beetle, desert spider mite, green peach aphid, leaf hoppers, melon aphid, pacific spider mite, spotted cucumber beetle, squash bug, squash vine borer, two spotted spider mite, western corn root worm, western spotted cucumber beetle, white fly, root-knot nematode; specific flower-fruit related traits, such as traits related to abscission, bitterness, blossom scar, fruit skin pattern, flesh color, flesh thickness, fruit diameter, fruit length, fruit rib, fruit shape, seed cavity color, fruit skin texture, spine color and fruit weight; specific type of plant growth habit; certain genetic loci, such as 6-phosphogluconate dehydrogenase loci, glucosephosphate isomerase loci, glutahtione reductase loci, isocitrate dehydrogenase loci, malic dehydrogenase loci, monosephosphate isomerase loci, peptidase with leucyl-alanine loci, peptidase loci, phosphoglucomutase loci, shikimate dehydrogenase loci); certain specific morphological traits, such as size/type of the blossom end fruit shape, size/type of cavity diameter, size/type of the blossom scar, ease of peduncle separation from fruit, ease of seed separation from flesh, external aroma, flesh color intensity, flesh flavor, flesh moisture, flower color, fruit skin corking, fruit skin glossiness, fruit splitting, fruit stem color, fruit stripes on blossom end, fruit volume, fruit width, internal aroma, internal color of skin, internode length, leaf color, leaf lobes, leaf shape, leaf size, number of fruits harvested per plant, number of seeds per fruit, seed coat color, seed shape, seed size, skin hardness of fruit), or certain preferred phenological traits, such as a desired time of maturity (based on accumulated heat units, days after planting, and/or day length), desired production related traits (e.g., 100 seed weight, flesh dry matter percent, fruit storage ability, fruit weight), and/or desired stress related traits (e.g., tolerance to drought, tolerance to salt, tolerance to low and high temperatures).

The resistance in the SLCV resistant cucurbit plants provided by the present invention is likely due to a single recessive locus in the genome based on genetic analysis. Without wishing to be bound by a particular theory, the single recessive locus is designated as slc-2 gene. The locus confirming resistance is linked to molecular markers which defining primers are in Table 8.

One skilled in the art will know how to clone the slc-2 gene using the SLCV resistant plants of the present invention. For example, one skilled in the art will be able to choose a suitable plant for crossing, generate a mapping population, and isolate polynucleotide of the slc-2 gene by map-based cloning or any other suitable methods (see, Varshney and Tuberisa, *Genomics-assisted crop improvement: Genomics application in crops, Volume 2 of Genomics-assisted Crop Improvement*, 2008, Springer, Loze and Wenzel, *Molecular marker systems in plant breeding and crop improvement*, 2007, Springer, ISBN. 3540740066 9783540740063; Kang, *Quantitative genetics, genomics, and plant breeding*, 2002, CABI, ISBN 0851996019, 9780851996011, each of which is incorporated herein by reference in its entirety). Such isolated polynucleotide sequence can be transferred into a recipient plant susceptible to SLCV through any breeding method described separately below, to make a new line that is resistant.

The isolated polynucleotide of slc-2 gene can be used in many aspects. In one embodiment, the nucleic acid sequence of the isolated slc-2 gene, or any function variant thereof, can be expressed in other plant species that are susceptible to SLCV, and wherein said species can not hybridize with cucurbit plants of the present invention. For example, said species is other *Cucurbitae* species, such as melon, cucumber, watermelon. In other embodiment, the isolated slc-2 gene, or fragment thereof can be used as probe to identify and/or isolate homologous genes in other plants.

Molecular Markers Linked to Resistance Gene slc-2

The inventors of the present invention also provide molecular markers that are linked to the SLCV resistant locus in the plants of the present invention.

At least 24 AFLP markers were found to be linked to SLCV resistant locus, and among which, markers E26/M48-179.61|P1, E26/M48-180.51|P2, and E26/M48-123.85|P2 are very close to the locus, and E26/M48-179.61|P1 and E26/M48-180.51|P2 are extremely close to the locus.

Molecular markers have proven to be of great value for increasing the speed and efficiency of plant breeding. Most traits of agronomic value, e.g. pest resistance, yield and the like, are difficult to measure, often requiring a full growth season and statistical analysis of field trial results. Interpretation of the data can be obscured or confused by environmental variables. Occasionally it has been possible for breeders to make use of conventional markers such as flower color which could be readily followed through the breeding process. If the desired gene or QTL is linked closely enough to a conventional marker, the likelihood of recombination occurring between them is sufficiently low that the gene or the QTL and the marker co-segregate throughout a series of crosses. The marker becomes, in effect, a surrogate for the gene or the QTL itself. Prior to the advent of molecular markers, the opportunities for carrying out marker-linked breeding were severely limited by the lack of suitable markers mapping sufficiently close to the desired trait. Map distance is simply a function of recombination frequency between two markers, genes, QTLs, genes and QTLS, or markers and genes or QTLs. Consequently, if a marker and a gene or a QTL map too far apart, too much recombination will occur during a series of crosses or self-pollinations such that the marker becomes no longer associated with the gene or the QTL. Having a wide selection of molecular markers available throughout the genetic map provides breeders the means to follow almost any desired trait through a series of crosses, by measuring the presence or absence of a marker linked to the gene or the QTL which affects that trait. The primary obstacle is the initial step of identifying a linkage between a marker and a gene or a QTL affecting the desired trait.

The inventors of the present invention identified molecular markers that are linked and in some instances that are tightly linked or very tightly linked to the resistance to SLCV, which is brings huge advantage in the breeding program targeting improve the resistance to SLCV in cucurbit plants. Molecular markers provide two additional operational advantages. First, since they exist as features of the plant DNA itself, they can be detected soon after germination, for example by analysis of leaf DNA of seedlings. Selection for plants carrying the marker can be performed at the seedling stage, thereby saving the space and energy formerly needed to grow large numbers of plants to maturity. Second, molecular markers do not depend on gene expression for detection. Their use is unlikely to lead to misleading results, such as can occur when environmental or other variables modify expression of conventional marker genes.

More molecular markers can be developed by using the SLCV resistant plants of the present invention. In general, as the map distance (expressed by the unit cM) between a molecular marker and a gene of interest becomes shorter, the marker and the gene are more closely localized to each other, and more likely to be inherited simultaneously; thus such markers are more useful. Methods of developing molecular markers are well known to one of ordinary skill in the art. The marks can be bi-allelic dominant, bi-allelic co-dominant, and/or multi-allelic co-dominant. The types of molecular markers that can be developed include, but are not limited to, restriction fragment length polymorphisms (RFLPs), isozyme markers, allele specific hybridization (ASH), amplified variable sequences of plant genome, self-sustained sequence replication, simple sequence repeat (SSR), single base-pair change (single nucleotide polymorphism, SNP), random amplification of polymorphic DNA (RAPDs), SSCPs (single stranded conformation polymorphisms); amplified fragment length polymorphisms (AFLPs) and microsatellites DNA.

Methods of developing molecular markers and their applications are described by Avise (Molecular markers, natural history, and evolution, Publisher: Sinauer Associates, 2004, ISBN 0878930418, 9780878930418), Srivastava et al. (Plant biotechnology and molecular markers, Publisher: Springer, 2004, ISBN1402019114, 9781402019111), and Vienne (Molecular markers in plant genetics and biotechnology, Publisher: Science Publishers, 2003), each of which is incorporated by reference in its entirety.

RAPD methods generally refer to methods of detecting DNA polymorphisms using differences in the length of DNAs amplified using appropriate primers. AFLP methods are essentially a combination of the above RFLP and RAPD methods, and refer to methods of selectively amplifying DNA restriction fragments using PCR to detect differences in their length, or their presence or absence. When RFLP markers are used as molecular markers of this invention, the identification methods of the present invention may be performed, for example, as below. First, DNA samples are prepared from a plant. Next, the prepared DNA sample is digested with restriction enzymes, the DNA fragments are separated based on their size, and the size of the detected DNA fragments is compared with a control. In the above method, if the separation pattern of separated test plant DNAs is the same type as the pattern of a SLCV resistant check plant (e.g., the cucurbit plants of the present invention), the plant is identified as being SLCV resistant. When an RAPD marker is used as a molecular marker of the invention, the identification methods of the present invention may be performed, for example, as follows: First, a DNA sample is prepared from a plant. Next, a PCR reaction is performed with primer DNAs, using the prepared DNA sample as a template. Amplified DNAs may be digested with restriction enzymes, as necessary. Then, the amplified DNA fragments are separated by electrophoresis, and the band pattern is compared with that of a SLCV resistant check plant (e.g., the cucurbit plants of the present invention). If the band patterns are the same type, the plant is identified as being a SLCV resistant plant. When an AFLP marker is used as a molecular marker of this invention, the identification methods of the invention may be performed as follows: First, a DNA sample is prepared from a plant. Next, the DNA sample is treated with a restriction enzyme, and then used as a template for an AFLP reaction. The amplified DNA fragments are then separated by size, and the detected DNA pattern is compared with that of a SLCV resistant check plant (e.g., the cucurbit plants of the present invention). One skilled in the art can easily perform AFLP reactions using optimal restriction enzymes and PCR primers. The DNA samples subjected to the identification methods of this invention are not particularly limited, but are normally genomic DNAs extracted from plants to be tested. The source of genomic DNAs is not particularly limited, and any plant tissue can be used for extraction. For example, leaves, roots, stems, seeds, endosperms, embryos, fruit, et al. can be used. In the present invention, the above DNA samples may be prepared (extracted) by any method known to one skilled in the art, for example, the CTAB method for DNA extraction. Furthermore, the identification methods of the present invention may be performed using more reliable markers, such as CAPS (cleaved amplified polymorphic sequence) and STS (sequence-tagged site) markers derived from the exact sequence analysis of AFLP markers.

The AFLP technology (Zabeau & Vos, 1993; Vos et al., 1995) has found widespread use in plant breeding and other field since its invention in the early nineties. This is due to several characteristics of AFLP, of which the most important is that no prior sequence information is needed to generate large numbers of genetic markers in a reproducible fashion, in addition, the principle of selective amplification, a cornerstone of AFLP, ensures that the number of amplified fragments can be brought in line with the resolution of the detection system, irrespective of genome size or origin.

Detection of AFLP fragments is commonly carried out by electrophoresis on slab-gels (Vos et al., AFLP: a new technique for DNA fingerprinting, Nucleic Acids Res. 1995 November 11; 23(21): 4407-4414, 1995) or capillary electrophoresis (van der Meulen et al., 2002). The majority of AFLP markers scored in this way represent polymorphisms occurring either in the restriction enzyme recognition sites used for AFLP template preparation or their flanking nucleotides covered by selective AFLP primers. The remainder of the AFLP markers are insertion/deletion polymorphisms occurring in the internal sequences of the restriction fragments and a very small fraction on single nucleotide substitutions occurring in small restriction fragments (<approximately 100 bp), which for these fragments cause reproducible mobility variations between both alleles which can be observed upon electrophoresis; these AFLP markers can be scored co-dominantly without having to rely on band intensities. Methods of developing AFLP markers are described in EP 534858, U.S. Pat. No. 6,045,994, WO2007114693 and Vos et al., each of which is hereby incorporated by reference in its entirety.

Thus, the present invention provides molecular markers that are linked to the resistance locus of the SLCV resistance plants of the present invention. As used herein, the term "linked" refers to the situation wherein the molecular marker and the SLCV resistant locus are segregating together over one or more generations. In some embodiments, the molecular marker and the SLCV resistant locus are segregating together in at least about 25% of a particular population in a particular generation. In one embodiment, the molecular marker can be any kind of marker described herein. For example, the molecular marker can be any AFLP markers, such as the AFLP markers which defining primers are listed in Table 8. The nucleotide sequences defining primers of the AFLP markers are shown in Table 8, or a complementary strand thereof can be used.

In one embodiment, the molecular markers of the present invention are closely linked to the SLCV resistant locus. As used herein, the phrase "closely linked" or "tightly linked" refers to the situation wherein the genetic distance between the molecular marker and the SLCV resistant locus is less than 2 centimorgan (cM). For example, the genetic distance between the marker and the slc-2 gene is about 2.0 cM, about 1.9 cM, about 1.8 cM, about 1.7 cM, about 1.6 cM, about 1.5 cM, about 1.4 cM, about 1.3 cM, about 1.2 cM, about 1.1 cM, about 1.0 cM, about 0.9 cM, about 0.8 cM, about 0.7 cM, about 0.6 cM, about 0.5 cM, about 0.4 cM, about 0.3 cM, about 0.2 cM, about 0.1 cM, or less than 0.1 cM. In one embodiment, the genetic marker is any type of markers described above, e.g., an AFLP marker. In further embodiments, the AFLP marker is any one of the molecular markers which defining primers are listed in Table 8.

The molecular markers identified herein can be used in many aspects of the present invention. For example, the molecular markers can facilitate the cloning of slc-2 gene and to assist a breeding program wherein the goal is to transfer SLCV resistance in the cucurbit lines of the present invention to other cucurbit lines. Detailed methods of molecular marker assisted selection/breeding is described by Wenzel (Molecular Marker Systems in Plant Breeding and Crop Improvement, Volume 55 of Biotechnology in Agriculture and Forestry, Publisher: Springer, 2007, ISBN 3540740066, 9783540740063), Xu (Molecular Plant Breeding, CABI, February 2010, ISBN 1845933923, 9781845933920), and Kang (Quantitative genetics, genomics, and plant breeding, CABI Publishing Series, 2002, ISBN 0851996019, 9780851996011), each of which is incorporated by reference in its entirety.

Methods of Producing Plants Resistant to SLCV

Any plant raised from the deposited seeds that is resistant to SLCV can be used to produce more cucurbit plants that are resistant to SLCV through plant breeding methods well known to those skilled in the art. The goal in general is to develop new, unique and superior varieties and hybrids. In some embodiments, selection methods, e.g., molecular marker assisted selection, can be combined with breeding methods to accelerate the process.

Choice of breeding or selection methods depends on the mode of plant reproduction, the heritability of the trait(s) being improved, and the type of cultivar used commercially (e.g., F1 hybrid cultivar, pure line cultivar, etc.). For highly heritable traits, a choice of superior individual plants evaluated at a single location will be effective, whereas for traits with low heritability, selection should be based on mean values obtained from replicated evaluations of families of related plants. Non-limiting breeding methods commonly include pedigree selection, modified pedigree selection, mass selection, recurrent selection, and backcross breeding.

The complexity of inheritance influences choice of the breeding method. Backcross breeding is used to transfer one or a few favorable genes for a heritable trait into a desirable cultivar. This approach has been used extensively for breeding disease-resistant cultivars, nevertheless, it is also suitable for the adjustment and selection of morphological characters, color characteristics and simply inherited quantitative characters. Various recurrent selection techniques are used to improve quantitatively inherited traits controlled by numerous genes. The use of recurrent selection in self-pollinating crops depends on the ease of pollination, the frequency of successful hybrids from each pollination and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested per se and in hybrid combination and compared to appropriate standards in environments representative of the commercial target area(s) for three years at least. The best lines are candidates for use as parents in new commercial cultivars; those still deficient in a few traits may be used as parents to produce new populations for further selection.

In one embodiment, said method comprises (i) crossing any one of the SLCV resistant plants of the present invention as a donor to a recipient plant line to create a F1 population;

(ii) evaluating SLCV resistance in the offsprings derived from said F1 population; and (iii) selecting offsprings that are resistant to SLCV.

To select SLCV resistant plants in the offsprings, a SLCV resistant control plant and/or a SLCV susceptible control plant are involved. The population of the control plant is also challenged with the virus strain, under similar environmental conditions and pest or pathogen pressure. Resistance level of the offsprings, plant tissue or plant cell thereof is compared to the resistance level of the control plant, plant tissue or plant cell.

In one embodiment, the evaluating step comprises visual observation to determine the severity of the virus infection, using a resistance scoring system. The resistance scoring system is well known in the art and is described elsewhere herein. Briefly, a resistance scoring system can be used to evaluate the resistance of a plant by signing a resistance score to a plant which ranges from 1 to 3, 1 to 5, or 1 to 10, et al., depending on the severity of the infection or symptoms. Alternatively, in the case wherein the breeders are focusing on certain symptoms such as the leaf curling of the plants, a scale of 0 to 5 can be used: a 0 would be attributed to plants showing no symptoms at all, 1 will be given to plants showing small curling on the older leaves, 2 for small curling on the older leaves and gaufrage on young leaves, 3 for small curling on young leaves, 4 for curling on young leaves and 5 for crispation and curling on young leaves. In addition to such visual evaluations, the evaluation can also be performed by determining the virus bio-density in a plant or plant part through molecular biological methods, such as protein hybridization (e.g., ELISA, measuring viral protein density) and/or nucleic acid hybridization (e.g., RT-PCR, measuring viral RNA density). Methods of detection have been described previously (see, Al-Musa et al., Detection and Molecular Characterization of Squash leaf curl virus (SLCV) in Jordan, *Journal of Phytopathology*, April 2008, Volume 156 Issue 5, Pages 311-316; El-Dougdoug et al., Identification of Squash Leaf Curl Virus (Egyptian Isolate), *Australian Journal of Basic and Applied Sciences,* 3(4): 3470-3478, 2009). Commercial SLCV detection kits are available (see, Neogen Europe Ltd., SLCV ELISA products, and SLCV IDENTIKIT™-Y/B).

A plant population is resistant if it has about 60%, about 65%, about 70%, about 75%, about 80%, about 85%, about 90%, about 95%, about 98%, about 99%, about 99.5%, or about 100% of the plants in the least symptomatic levels of 0, 1, and 2 using the leaf curling rating system as described in more detail elsewhere herein. In one embodiment, a plant population is some resistant to the virus if it has greater than about 60% of the plants in the least symptomatic levels of 0, 1, and 2. In one embodiment, a plant population is obviously resistant to the virus if it has great than about 70% of the plants in the least symptomatic levels of 0, 1, and 2. In one embodiment, a plant population is highly resistant to the virus if it has greater than about 80% of the plants in the least symptomatic levels of 0, 1, and 2. In one embodiment, a plant population is extremely resistant to the virus if it has greater than about 90% of the plants in the least symptomatic levels of 0, 1, and 2. A plant population is susceptible if it has about 50%, about 55%, about 60%, about 65%, about 70%, about 75%, about 80%, about 85%, about 90%, about 95%, about 98%, about 99%, about 99.5%, or about 100% of the plants in the most symptomatic levels of 3, 4, and 5 using the leaf curling rating system as described elsewhere herein. In one embodiment, a plant population is some susceptible to the virus if it has greater than about 60% of the plants in the most symptomatic levels of 3, 4, and 5. In one embodiment, a plant population is obviously susceptible to the virus if it has great than about 70% of the plants in the most symptomatic levels of 3, 4, and 5. In one embodiment, a plant population is highly susceptible to the virus if it has greater than about 80% of the plants in the most symptomatic levels of 3, 4, and 5. In one embodiment, a plant population is extremely susceptible to the virus if it has greater than about 90% of the plants in the most symptomatic levels of 3, 4, and 5.

In another embodiment, said evaluating step comprises one or more molecular biological tests of virus density in the plants. In one embodiment, said molecular biological tests comprise testing the density of SLCV-specific nucleic acid sequence and/or SLCV-specific protein. For example, the molecular biological test can involve probe hybridization and/or amplification of nucleic acid (e.g., measuring viral nucleic acid density by Northern or Southern hybridization, RT-PCR) and/or immunological detection (e.g., measuring viral protein density, such as precipitation and agglutination tests, ELISA (e.g., Lateral Flow test or DAS-ELISA), Western blot, RIA, immunogod labeling, immunosorbent electron microscopy (ISEM), and/or dot blot). For example, a plant may be resistant to a virus strain if it has a virus nucleic acid and/or protein density that is about 50%, about 40%, about 30%, about 20%, about 10%, about 5%, about 2%, about 1%, about 0.1%, about 0.01%, about 0.001%, or about 0.0001% of the virus nucleic acid and/or protein density in a susceptible plant.

The procedure to perform a nucleic acid hybridization, an amplification of nucleic acid (e.g., RT-PCR) or an immunological detection (e.g., precipitation and agglutination tests, ELISA (e.g., Lateral Flow test or DAS-ELISA), Western blot, RIA, immunogod labeling, immunosorbent electron microscopy (ISEM), and/or dot blot tests) are performed as described elsewhere herein and well-known by one skilled in the art.

In one embodiment, the evaluating step comprise RT-PCR (semi-quantitative or quantitative), wherein SLCV-specific primers are used to amplify one or more SLCV-specific nucleic acid sequences. In one embodiment, said SLCV-specific nucleic acid sequences are from the same gene of SLCV. In another embodiment, said SLCV-specific nucleic acid sequences are from different genes of SLCV. In one embodiment, said RT-PCT is a real-time RT-PCT.

In another embodiment, the evaluating step comprises immunological detection (e.g., precipitation and agglutination tests, ELISA (e.g., Lateral Flow test or DAS-ELISA), Western blot, RIA, immunogod labeling, immunosorbent electron microscopy (ISEM), and/or dot blot), wherein one or more SLCV-specific antibodies are used to detect one or more SLCV-specific proteins. In one embodiment, said SLCV-specific antibody is selected from the group consisting of polyclonal antibodies, monoclonal antibodies, and combination thereof. In one embodiment, said SLCV-specific protein is SLCV coat protein.

Reverse Transcription Polymerase Chain Reaction (RT-PCR) can be utilized in the present invention to determine the virus RNA density in a plant. It is a variant of polymerase chain reaction (PCR), a laboratory technique commonly used in molecular biology to generate many copies of a DNA sequence, a process termed "amplification". In RT-PCR, however, RNA strand is first reverse transcribed into its DNA complement (complementary DNA, or cDNA) using the enzyme reverse transcriptase, and the resulting cDNA is amplified using traditional or real-time PCR.

RT-PCR utilizes a pair of primers, which are complementary to a defined sequence on each of the two strands of the cDNA. These primers are then extended by a DNA polymerase and a copy of the strand is made after each cycle, leading to logarithmic amplification.

RT-PCR includes three major steps. The first step is the reverse transcription (RT) where RNA is reverse transcribed to cDNA using a reverse transcriptase and primers. This step is very important in order to allow the performance of PCR since DNA polymerase can act only on DNA templates. The RT step can be performed either in the same tube with PCR (one-step PCR) or in a separate one (two-step PCR) using a temperature between 40° C. and 50° C., depending on the properties of the reverse transcriptase used.

The next step involves the denaturation of the dsDNA at 95° C., so that the two strands separate and the primers can bind again at lower temperatures and begin a new chain reaction. Then, the temperature is decreased until it reaches the annealing temperature which can vary depending on the set of primers used, their concentration, the probe and its concentration (if used), and the cations concentration. The main consideration, of course, when choosing the optimal annealing temperature is the melting temperature (Tm) of the primers and probes (if used). The annealing temperature chosen for a PCR depends directly on length and composition of the primers. This is the result of the difference of hydrogen bonds between A-T (2 bonds) and G-C (3 bonds). An annealing temperature about 5 degrees below the lowest Tm of the pair of primers is usually used.

The final step of PCR amplification is the DNA extension from the primers which is done by the thermostable Taq DNA polymerase usually at 72° C., which is the optimal temperature for the polymerase to work. The length of the incubation at each temperature, the temperature alterations and the number of cycles are controlled by a programmable thermal cycler. The analysis of the PCR products depends on the type of PCR applied. If a conventional PCR is used, the PCR product is detected using agarose gel electrophoresis and ethidium bromide (or other nucleic acid staining).

Conventional RT-PCR is a time-consuming technique with important limitations when compared to real time PCR techniques. This, combined with the fact that ethidium bromide has low sensitivity, yields results that are not always reliable. Moreover, there is an increased cross-contamination risk of the samples since detection of the PCR product requires the post-amplification processing of the samples. Furthermore, the specificity of the assay is mainly determined by the primers, which can give false-positive results. However, the most important issue concerning conventional RT-PCR is the fact that it is a semi or even a low quantitative technique, where the amplicon can be visualized only after the amplification ends.

Real time RT-PCR provides a method where the amplicons can be visualized as the amplification progresses using a fluorescent reporter molecule. There are three major kinds of fluorescent reporters used in real time RT-PCR, general non specific DNA Binding Dyes such as SYBR Green I, TaqMan Probes and Molecular Beacons (including Scorpions).

The real time PCR thermal cycler has a fluorescence detection threshold, below which it cannot discriminate the difference between amplification generated signal and background noise. On the other hand, the fluorescence increases as the amplification progresses and the instrument performs data acquisition during the annealing step of each cycle. The number of amplicons will reach the detection baseline after a specific cycle, which depends on the initial concentration of the target DNA sequence. The cycle at which the instrument can discriminate the amplification generated fluorescence from the background noise is called the threshold cycle (Ct). The higher is the initial DNA concentration, the lower its Ct will be.

In one embodiment, complete chromosomes of the donor plant are transferred. For example, the SLCV resistant plant can serve as a male or female parent in a cross pollination to produce resistant offspring plants, wherein by receiving the genomic material from the resistant donor plant, the offspring plants are resistant to SLCV. Alternatively, a resistant plant can be cloned or produced via tissue culture so as to produce additional plants with resistance.

In one method for producing a SLCV resistant plant, agoinoculation technique can be applied. For example, Agrobacteria harboring the ssDNA genome or part of the genome of SLCV that have been inserted in a binary T-DNA vector can be efficiently used for infection of plant population. More details about this technique are demonstrated in Yousif et al. (Sources of resistance to Watermelon Chlorotic Stunt Virus in melon. 2007, Plant Breeding 126, 422-427). Generally speaking, Agrobacterium strains containing T-DNA vectors which comprise the SLCV virus sequences are raised from medium, collected by centrifugation, resuspended in suitable solution, and immediately used for inoculation. The bacteria can be injected into plants of certain development stages by pricking the petioles of cut leaves with syringe. The agro-inoculated plants are then kept in a growth chamber maintained at preferred temperature and humidity. Symptoms are recorded after the inoculation, or alternatively, presence/absence of the SLCV genomic DNA or SLCV specific protein was assessed by hybridization with labeled DNA probe or by antibodies. As a result, resistant or susceptible plants can be identified.

In another method for producing a SLCV resistant plant, protoplast fusion can also be used for the transfer of resistance-conferring genomic material from a donor plant to a recipient plant. Protoplast fusion is an induced or spontaneous union, such as a somatic hybridization, between two or more protoplasts (cells of which the cell walls are removed by enzymatic treatment) to produce a single bi- or multi-nucleate cell. The fused cell, that may even be obtained with plant species that cannot be interbred in nature, is tissue cultured into a hybrid plant exhibiting the desirable combination of traits. More specifically, a first protoplast can be obtained from a plant line that is resistant to SLCV. For example, a protoplast from a SLCV-resistant (melon, watermelon, squash or cucumber) line may be used. A second protoplast can be obtained from a susceptible second plant line, optionally from another plant species or variety, preferably from the same plant species or variety, that comprises commercially desirable characteristics, such as, but not limited to disease resistance, insect resistance, valuable fruit characteristics, etc. The protoplasts are then fused using traditional protoplast fusion procedures, which are known in the art to produce the cross.

Alternatively, embryo rescue may be employed in the transfer of resistance-conferring genomic material from a donor plant to a recipient plant. Embryo rescue can be used as a procedure to isolate embryo's from crosses wherein plants fail to produce viable seed. In this process, the fertilized ovary or immature seed of a plant is tissue cultured to create new plants (see Pierik, 1999, *In vitro culture of higher plants*, Springer, ISBN 079235267x, 9780792352679, which is incorporated herein by reference in its entirety).

In addition, in one embodiment, a method for producing a SLCV resistant plant comprises grafting a susceptible recipient plant onto resistant rootstocks of SLCV resistant plants, which is proved to be an effective methodology developed for intensive cultivation in the Far East (Lee and Oda, 2003, Grafting of herbaceous vegetable and ornamental crops, *Hort. Rev.* 28:61-124).

As described before, the recipient line can be an elite line having certain favorite traits. In one embodiment, the elite line is resistant to SLCV due to a different genetic cause other than slc-2 gene. When crossed together, different loci may provide quantitatively additive effect in terms of resistance to SLCV. In that case, QTL mapping can be involved to facilitate the breeding process.

A QTL (quantitative trait locus) mapping can be applied to determine the parts of the donor plant's genome conferring the SLCV resistance, and facilitate the breeding methods. Inheritance of quantitative traits or polygenic inheritance refers to the inheritance of a phenotypic characteristic that varies in degree and can be attributed to the interactions between two or more genes and their environment. Though not necessarily genes themselves, quantitative trait loci (QTLs) are stretches of DNA that are closely linked to the genes that underlie the trait in question. QTLs can be molecularly identified to help map regions of the genome that contain genes involved in specifying a quantitative trait. This can be an early step in identifying and sequencing these genes.

Typically, QTLs underlie continuous traits (those traits that vary continuously, e.g. level of resistance to virus) as opposed to discrete traits (traits that have two or several character values, e.g. smooth vs. wrinkled peas used by Mendel in his experiments). Moreover, a single phenotypic trait is usually determined by many genes. Consequently, many QTLs are associated with a single trait.

A quantitative trait locus (QTL) is a region of DNA that is associated with a particular phenotypic trait—these QTLs are often found on different chromosomes. Knowing the number of QTLs that explains variation in the phenotypic trait tells about the genetic architecture of a trait. It may tell that plant resistance to virus of the present invention is controlled by many genes of small effect, or by a few genes of large effect.

Another use of QTLs is to identify candidate genes underlying a trait. Once a region of DNA is identified as contributing to a phenotype, it can be sequenced. The DNA sequence of any genes in this region can then be compared to a database of DNA for genes whose function is already known.

In a recent development, classical QTL analyses are combined with gene expression profiling i.e. by DNA microarrays. Such expression QTLs (e-QTLs) describes cis- and trans-controlling elements for the expression of often disease-associated genes. Observed epistatic effects have been found beneficial to identify the gene responsible by a cross-validation of genes within the interacting loci with metabolic pathway- and scientific literature databases.

QTL mapping is the statistical study of the alleles that occur in a locus and the phenotypes (physical forms or traits) that they produce (see, Meksem and Kahl, *The handbook of plant genome mapping: genetic and physical mapping*, 2005, Wiley-VCH, ISBN 3527311165, 9783527311163). Because most traits of interest are governed by more than one gene, defining and studying the entire locus of genes related to a trait gives hope of understanding what effect the genotype of an individual might have in the real world.

Statistical analysis is required to demonstrate that different genes interact with one another and to determine whether they produce a significant effect on the phenotype. QTLs identify a particular region of the genome as containing a gene that is associated with the trait being assayed or measured. They are shown as intervals across a chromosome, where the probability of association is plotted for each marker used in the mapping experiment.

To begin, a set of genetic markers must be developed for the species in question. A marker is an identifiable region of variable DNA. Biologists are interested in understanding the genetic basis of phenotypes (physical traits). The aim is to find a marker that is significantly more likely to co-occur with the trait than expected by chance, that is, a marker that has a statistical association with the trait. Ideally, they would be able to find the specific gene or genes in question, but this is a long and difficult undertaking. Instead, they can more readily find regions of DNA that are very close to the genes in question. When a QTL is found, it is often not the actual gene underlying the phenotypic trait, but rather a region of DNA that is closely linked with the gene.

For organisms whose genomes are known, one might now try to exclude genes in the identified region whose function is known with some certainty not to be connected with the trait in question. If the genome is not available, it may be an option to sequence the identified region and determine the putative functions of genes by their similarity to genes with known function, usually in other genomes. This can be done using BLAST, an online tool that allows users to enter a primary sequence and search for similar sequences within the BLAST database of genes from various organisms.

Another interest of statistical geneticists using QTL mapping is to determine the complexity of the genetic architecture underlying a phenotypic trait. For example, they may be interested in knowing whether a phenotype is shaped by many independent loci, or by a few loci, and do those loci interact. This can provide information on how the phenotype may be evolving.

Molecular markers are used for the visualization of differences in nucleic acid sequences. This visualization is possible due to DNA-DNA hybridization techniques (RFLP) and/or due to techniques using the polymerase chain reaction (e.g. STS, microsatellites, AFLP). All differences between two parental genotypes will segregate in a mapping population based on the cross of these parental genotypes. The segregation of the different markers may be compared and recombination frequencies can be calculated. The recombination frequencies of molecular markers on different chromosomes are generally 50%. Between molecular markers located on the same chromosome the recombination frequency depends on the distance between the markers. A low recombination frequency corresponds to a low distance between markers on a chromosome. Comparing all recombination frequencies will result in the most logical order of the molecular markers on the chromosomes. This most logical order can be depicted in a linkage map (Paterson, 1996). A group of adjacent or contiguous markers on the linkage map that is associated to a reduced disease incidence and/or a reduced lesion growth rate pinpoints the position of a QTL.

The nucleic acid sequence of a QTL may be determined by methods known to the skilled person. For instance, a nucleic acid sequence comprising said QTL or a resistance-conferring part thereof may be isolated from a SLCV-resistant donor plant by fragmenting the genome of said plant and selecting those fragments harboring one or more markers indicative of said QTL. Subsequently, or alternatively, the marker sequences (or parts thereof) indicative of said QTL may be used as (PCR) amplification primers, in order to amplify a nucleic acid sequence comprising said QTL from a genomic nucleic acid sample or a genome fragment obtained from said plant. The amplified sequence may then be purified in order to obtain the isolated QTL. The nucleotide sequence of the QTL, and/or of any additional markers comprised therein, may then be obtained by standard sequencing methods.

One or more such QTLs associated with the resistance to SLCV in a donor plant can be transferred to a recipient plant that is susceptible to SLCV to make it become resistant through any transferring and/or breeding methods.

In one embodiment, an advanced backcross QTL analysis (AB-QTL) is used to discover the nucleotide sequence or the QTLs responsible for the resistance of a plant. Such method was proposed by Tanksley and Nelson in 1996 (Tanksley and Nelson, 1996, Advanced backcross QTL analysis: a method for simultaneous discovery and transfer of valuable QTL from un-adapted germplasm into elite breeding lines. *Theor Appl Genet* 92:191-203) as a new breeding method that integrates the process of QTL discovery with variety development, by simultaneously identifying and transferring useful QTL alleles from un-adapted (e.g., land races, wild species) to elite germplasm, thus broadening the genetic diversity available for breeding. A non-limiting exemplary scheme of AB-QTL mapping strategy is shown in FIG. 2. AB-QTL strategy was initially developed and tested in tomato, and has been adapted for use in other crops including rice, maize, wheat, pepper, barley, and bean. Once favorable QTL alleles are detected, only a few additional marker-assisted generations are required to generate near isogenic lines (NILs) or introgression lines (ILs) that can be field tested in order to confirm the QTL effect and subsequently used for variety development.

Isogenic lines in which favorable QTL alleles have been fixed can be generated by systematic backcrossing and introgressing of marker-defined donor segments in the recurrent parent background. These isogenic lines are referred as near isogenic lines (NILs), introgression lines (ILs), backcross inbred lines (BILs), backcross recombinant inbred lines (BCRIL), recombinant chromosome substitution lines (RC-SLs), chromosome segment substitution lines (CSSLs), and stepped aligned inbred recombinant strains (STAIRSs). An introgression line in plant molecular biology is a line of a crop species that contains genetic material derived from a similar species. ILs represent NILs with relatively large average introgression length, while BILs and BCRILs are backcross populations generally containing multiple donor introgressions per line. As used herein, the term "introgression lines or ILs" refers to plant lines containing a single marker defined homozygous donor segment, and the "pre-ILs" refers to lines which still contain multiple homozygous and/or heterozygous donor segments.

To enhance the rate of progress of introgression breeding, a genetic infrastructure of exotic libraries can be developed. Such an exotic library comprises of a set of introgression lines, each of which has a single, possibly homozygous, marker-defined chromosomal segment that originates from a donor exotic parent, in an otherwise homogenous elite genetic background, so that the entire donor genome would be represented in a set of introgression lines. A collection of such introgression lines is referred as libraries of introgression lines or IL libraries (ILLs). The lines of an ILL cover usually the complete genome of the donor, or the part of interest. Introgression lines allow the study of quantitative trait loci, but also the creation of new varieties by introducing exotic traits. High resolution mapping of QTL using ILLs enable breeders to assess whether the effect on the phenotype is due to a single QTL or to several tightly linked QTL affecting the same trait. In addition, sub-ILs can be developed to discover molecular markers which are more tightly linked to the QTL of interest, which can be used for marker-assisted breeding (MAB). Multiple introgression lines can be developed when the introgression of a single QTL is not sufficient to result in a substantial improvement in agriculturally important traits (Gur and Zamir, Unused natural variation can lift yield barriers in plant breeding, 2004, *PLoS Biol.*; 2(10): e245).

Breeding Methods

Open-Pollinated Populations.

The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes for flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are basically two primary methods of open-pollinated population improvement. First, there is the situation in which a population is changed en masse by a chosen selection procedure. The outcome is an improved population that is indefinitely propagable by random-mating within itself in isolation. Second, the synthetic variety attains the same end result as population improvement but is not itself propagable as such; it has to be reconstructed from parental lines or clones. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative Genetics in Maize Breeding*, Iowa State University Press (1981); and, Jensen, *Plant Breeding Methodology*, John Wiley & Sons, Inc. (1988).

Mass Selection.

In mass selection, desirable individual plants are chosen, harvested, and the seed composited without progeny testing to produce the following generation. Since selection is based on the maternal parent only, and there is no control over pollination, mass selection amounts to a form of random mating with selection. As stated above, the purpose of mass selection is to increase the proportion of superior genotypes in the population.

Synthetics.

A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (Vicia) or clones, as in herbage grasses, clovers and alfalfa, makes no difference in principle. Parents are selected on general combining ability, sometimes by test crosses or toperosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enters a synthetic varies widely. In practice, numbers of parental lines range from 10 to several hundred, with 100-200 being the average. Broad based synthetics formed from 100 or more clones would be expected to be more stable during seed multiplication than narrow based synthetics.

Hybrids. A hybrid is an individual plant resulting from a cross between parents of differing genotypes. Commercial hybrids are now used extensively in many crops, including corn (maize), sorghum, sugarbeet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

The production of hybrids is a well-developed industry, involving the isolated production of both the parental lines and the hybrids which result from crossing those lines. For a detailed discussion of the hybrid production process, see, e.g., Wright, *Commercial Hybrid Seed Production* 8:161-176, In Hybridization of Crop Plants.

Bulk Segregation Analysis (BSA).

BSA, a.k.a. bulked segregation analysis, or bulk segregant analysis, is a method described by Michelmore et al. (Michelmore et al., 1991, Identification of markers linked to disease-resistance genes by bulked segregant analysis: a rapid method to detect markers in specific genomic regions by using segregating populations. *Proceedings of the National Academy of Sciences*, USA, 99: 9828-9832) and Quarrie et al. (Quarrie et al., Bulk segregant analysis with molecular markers and its use for improving drought resistance in maize, 1999, *Journal of Experimental Botany*, 50(337):1299-1306).

For BSA of a trait of interest, parental lines with certain different phenotypes are chosen and crossed to generate F2, doubled haploid or recombinant inbred populations with QTL analysis. The population is then phenotyped to identify individual plants or lines having high or low expression of the trait. Two DNA bulks are prepared, one from the individuals having one phenotype (e.g., resistant to virus), and the other from the individuals having reversed phenotype (e.g., susceptible to virus), and analyzed for allele frequency with molecular markers. Only a few individuals are required in each bulk (e.g., 10 plants each) if the markers are dominant (e.g., RAPDs). More individuals are needed when markers are co-dominant (e.g., RFLPs). Markers linked to the phenotype can be identified and used for breeding or QTL mapping.

It should be understood that the examples and embodiments described herein are for illustrative purposes only and that various modifications or changes in light thereof will be suggested to persons skilled in the art and are to be included within the spirit and purview of this application.

EXAMPLES

Example 1

Identification of SLCV Resistant Starting Material

Several *Cucurbita moschata* lines were evaluated under different geographical areas in open field trials (natural infections conditions). Lines included 'CT1', 'CT2', 'CT3', 'CT4', 'CT5', and 'WSXP1030'(also as known as the 'Ns' line). 'CT6' was used as a susceptible *C. moschata* check or control line.

1.1 Evaluation of Different Tolerance Resistance Sources in Open Fields Trials, in Natural Infection Conditions Locations and dates of planting were chosen because they were known to have a high probability of severe natural infection of SLCV.

Trial 1: Jordan Trial

The field in which the trial was conducted is near Amman, Jordan. Young plants were transplanted in the first week of a July. Two replicates of each lines to be evaluated were planted and each replicate had 10 plants. The evaluation was done on September 12 of the same year, using a scale from 0 to 5, wherein "0" is without any symptoms and "5" is very symptomatic (i.e., susceptible) plants. Detailed scale is explained below:

0=no symptom

1=small curling on old leaves

2=small curling and gauffrage on young leaves

3=small curling on young leaves

4=curling on young leaves

5=crispation and curling on young leaves

The evaluation results are provided in Table 2 below. Susceptible check plants ('CT6') were destroyed by virus, and 100% infection was observed on checks, while 'CT1' to 'CT5' and 'WSXP1030' plants all gave certain resistance. The resistance in 'WSXP1030' equaled the one in 'CT3' and both were superior to the one found in 'CT2' which resembled the one found in 'CT4' (i.e., resistance of ('WSXP1030'='CT3')>('CT2'≈'CT4')>'CT6').

To make sure the disease was not caused by other infections, the inventors tested several viruses transmitted by aphids using ELISA, including Cucumber mosaic virus (CMV), Watermelon mosaic virus (WMV), Moroccan Watermelon Mosaic Potyvirus (MWMV), Papaya ringspot virus (PRSV), and Zucchini yellow mosaic virus (ZYMV), and did not detect any.

TABLE 2

SLCV Infection - Jordan Trial Result

| Rep 1 (Rep. No.) | Rep 2 (Rep. No.) | Designation | Rep1 virus rating value | Rep2 virus rating value | Mean virus rating value |
|---|---|---|---|---|---|
| 201 | 301 | CT1 | 2 | 3 | 2.5 |
| 202 | 302 | CT2 | 0 | 1 | 0.5 |
| 203 | 303 | WSXP1030 | 0 | 0 | 0 |
| 204 | 304 | CT3 | 0 | na | na |
| 205 | 305 | CT4 | 0 | na | na |
| 206 | 306 | CT5 | 2 | 0 | 1 |
| 207 | 307 | CT6 | 5 | na | na |

"na" means the result is not available, for example, due to lack of germination or unavailability of seed.

Trial 2: Israeli Trial

The field in which the trial was conducted is in Mivhor, Israel. Young plants were transplanted in the first week of a July 5th. Three replicates of each line to be evaluated were planted and each replicate had 10 plants. The evaluation was done on September 13 of the same year, using a scale from 0 to 5, wherein "0" is without any symptoms and "5" indicates very symptomatic plants.

The evaluation results are provided in Table 3 below. Growth of susceptible check plants ('CT6') were stopped by virus, and 100% infection was observed on checks; while 'CT1' to 'CT5' and 'WSXP1030' plants all demonstrated some level of resistance. The most resistant line was 'WSXP1030', and a similar level was observed in CT3 and CT5. Virus symptoms on 'CT4' were obvious, but likely not due to SLCV, since the symptoms were new and different from symptoms caused by SLCV, and no SLCV was detected on 'CT4' plants. The new symptoms were likely not attributed to any virus.

TABLE 3

SLCV Infection - Israeli Trial Result

| Rep 1 (Rep. No.) | Rep 2 (Rep. No.) | Rep 3 (Rep. No.) | Designation | Rep1 virus rating value | Rep2 virus rating value | Rep3 virus rating value | Mean virus rating value |
|---|---|---|---|---|---|---|---|
| 201 | 301 | 401 | CT1 | 3 | na | na | na |
| 202 | 302 | 402 | CT2 | 1 | 1 | na | na |
| 203 | 303 | 403 | WSXP1030 | 0 | 0 | 0 | 0 |
| 204 | 304 | 404 | CT3 | 0 | 0 | 0 | 0 |
| 205 | 305 | 405 | CT4 | 3 | 3.5 | 3.5 | 3.3 |
| 206 | 306 | 406 | CT5 | 0 | 0 | 0 | 0 |
| 207 | 307 | 407 | CT6 | 4 | na | na | na |

"na" means the result is not available, for example, due to lack of germination or unavailability of seed.

Trial 3: Mexican Trial (a)

The field in which the trial was conducted is located in a grower field of Izucar (near Puebla), Mexico. Young plants were transplanted on February 13th. Two replicates of each line to be evaluated were planted and each replicate had 10 plants. The evaluation was done the on April 19 of the same year, using a scale from 0 to 5, wherein "0" is without any symptoms and "5" is very symptomatic plants.

Since the susceptible check plants were not attached by virus, which indicated that no SLCV infection was observed, no conclusion can be made based on this trial.

Trial 4: Mexican Trial (b)

The field in which the trial was conducted is located in Los Mochis, Mexico. Young plants were transplanted on February 20th. Two replicates of each line to be evaluated were planted and each replicate had 10 plants. The evaluation was done the on April 17 of the same year, using a scale from 0 to 5, wherein "0" is without any symptoms and "5" is very symptomatic plants.

The data of this trial indicates that 'CT3', 'CT4' and 'WSXP1030' displayed good or very good resistance to virus infection, as shown in Table 4, below. Some Papaya ringspot virus (PRSV) was detected, suggesting the field was not optimum for testing SLCV.

Table 4 below summarizes the trials in Jordan, Israel, and Los Mochis. The inventors concluded that 'CT3', 'CT4' and 'WXSP1030' are consistently resistant to SLCV, and can be used for further analysis.

TABLE 4

Summary of Open Field Evaluation Trials

| | Amman, Jordan | Mivhor, Israel | Los Mochis, Mexico |
|---|---|---|---|
| CT1 | Not int* | Not int | Not int |
| CT2 | Good | Not int | Not int |
| CT3 | Very Good | Very Good | Good |
| CT4 | Good | New virus? | Very Good |
| CT5 | Not int | Very Good | Not int |
| CT6 | Susceptible | Susceptible | Susceptible |
| WXSP1030 | Very Good | Very Good | Good |

*"Not int" means the line is not interesting for further analysis

Trial 5: Comparison of 'CT3', 'CT4' and 'WSXP 1030' to Other Squash Cultivars

'CT3', 'CT4' and 'WSXP1030' were next tested in a trial against SLCV infection along with several commercial squash cultivars as check lines for comparison. The trial was conducted in Los Mochis, Mexico, using the same strategy as described above.

The test results in Table 5 clearly suggest that 'CT3', 'CT4' and 'WSXP1030' have far more resistance than the commercial cultivars against SLCV infection.

TABLE 5

Open Field Trial- Comparison to Commercial Cultivars

| CODE | No. | Leaf Curling |
|---|---|---|
| CT3 | 1 | 0 |
| CT4 | 2 | 0 |
| WSXP1030 | 3 | 0 |
| Topazio | 4 | 2 |
| FES | 5 | 4 |
| CLUGO | 6 | 5 |
| Hurakan | 7 | 4 |
| Linda | 8 | 5 |
| Citlali | 9 | 2 |

Leaf Curling Scale:
0 = no symptom
1 = small curling on old leaves
2 = small curling and gauffrage on young leaves
3 = small curling on young leaves
4 = curling on young leaves
5 = crispation and curling on young leaves Example 2

Allelism Tests

Three sources stood out for resistance to SLCV from the field test trials conducted under natural infection conditions as described in Example 1: 'WSXP1030', 'CT3' and 'CT4'.

Allelism tests have been performed between these 3 lines to see if the same genes are involved in the resistance to SLCV. The test setup and results are shown in FIG. 1.

F2 populations were derived from the crosses of 'Ns'× 'CT3' and 'Ns'×'CT4' were analyzed with resistant check lines ('Ns' and 'CT4' lines) and susceptible check line 'Waltham Butternut'. The susceptible check, 'Waltham Butternut', had only 2 apparent escapes, and most plants had early and severe symptoms. The resistant checks, 'Ns' and 'CT4', did not have any susceptible plants, although there were some with intermediate symptoms (corresponding to 2 or 3 on the 0 to 5 scale). Without wishing to be bound by theory, the intermediate symptoms may be due to some genetic variations, variations in seedling emergence or vigor, variations in inoculation, or a combination of one or more of these factors. It is not unusual to see some plants with intermediate symptoms even when testing advanced lines that should be genetically uniform. 'CT3' was not included as a check since at the time the test was conducted, there was not enough 'CT3' seed available. Most of the intermediate plants had late appearing symptoms. Without wishing to be bound by a particular theory, one explanation for the late appearing symptoms is that the growth of the plants may have slowed due to the volume of the pot they were growing in. This allowed the virus to "catch up" with the growth of the plants. This phenomenon has also been observed by breeders working with other viruses. These late symptoms were not caused by other viruses because this work was done in the greenhouse under controlled conditions.

The inventors concluded that 'Ns' and 'CT4' have the same gene for resistance since there were no susceptible and no more intermediates than the resistant checks in the F2. From this experiment only, it was not clear if the SLCV resistant gene(s) in 'Ns' and 'CT3' are the same. There were 2 plants in the F2 that have been rated as susceptible, but their symptoms did not appear as early as those of the susceptible check and the breeders did not have 'CT3' itself as a check.

Molecular markers linked to SLCV resistance were next used to further address the question if the same gene is responsible for the SLCV resistance in 'CT3', 'CT4' and 'Ns'lines. If identical genes are involved in all sources, the marker identified will work on all genetic material, regardless of the resistance source.

Example 3

Identification of the Nature of the Resistance (Single Recessive Gene)

An SLCV susceptible inbred line was crossed with an SLCV resistant F2 individual to generate a F1 population. The SLCV resistant F2 individual was derived from a cross between a susceptible line and a segregating backcross (about 80-90% C. pepo) derived from Ns. An individual of this F1 was selfed to create an F2 population. The individuals within this F2 were selfed to create F3 families that were phenotyped in greenhouse.

The F3 families were phenotyped and classified into 3 different groups: resistant, segregating and susceptible. Resistant plants have very few or no symptoms, segregating plants have mild symptoms (corresponding to 2 or 3 on the 0 to 5 scale), and susceptible plants have severe symptoms (corresponding to 4 or 5 on the 0 to 5 scale).

Each family had a population size of 12, or less if bad germ, and, after the susceptible plants started showing symptoms, each plant was rated for disease and then rated again 5 days later. Based on these results, each F3 population was classified into resistant, segregating, and susceptible categories. Of the 28 F3 populations, 8 were resistant, 13 were segregating, and 7 were susceptible. This result is in agreement with the expected 1R:2Sg:1S ratio and confirms that a single recessive gene is involved.

Other resistance lines were tested concomitantly with the plants used for the identification for the nature of the gene. Among these plants were 'Topazio', from Syngenta and various lines developed by Sergio Garza of the Universidad de Sonora in Hermosillo, all together known for presenting some degree of resistance to SLCV. In all such trial, the 'Topazio' and the Sergio Garzas' material were consistently rated as moderate/intermediate resistance (IR) while the resistant material developed by Harris Moran was rated as high/standard resistant (HR).

Example 4

Marker Development

As used herein, the term "molecular marker" refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), insertion mutations, microsatellite markers (SSRs), sequence-characterized amplified regions (SCARs), cleaved amplified polymorphic sequence (CAPS) markers or isozyme markers or combinations of the markers described herein which defines a specific genetic and chromosomal location.

The inventors undertook this experiment to identify markers linked to the new SLCV resistance gene slc-2 in squash. The inventors utilized AFLP (see, AFLP: a new technique for DNA fingerprinting, Vos et al., 1995 Nucleic Acid Research., 23: 4407-4414) combined with Bulk Segregant Analysis (BSA) (Michelmore et al., 1991, Identification of markers linked to disease-resistance genes by bulked segregant analysis: a rapid method to detect markers in specific genomic regions by using segregating populations, Proc. Natl. Acad. Sci. USA. 1991 Nov. 1; 88(21): 9828-32) to develop molecular markers linked to the resistance gene.

In the context of AFLP markers named herein the markers indicate a squash-specific DNA sequence flanked by two AFLP-primers, which primers consist of "core primers" E and M, corresponding with the restriction sites of the restriction enzymes EcoRI and Mse1, (Vos et al., 1995; Bai et al. 2003) followed by 2 or 3 extra selective bases as indicated, each followed by a two-digit code identifying the selective nucleotides by which the "core primer" is extended (for code see the list below). E16/M50-244 represents a marker obtained by using amplification primers EcoRI+CC and MseI+CAT to produce a fragment having a total length of 244 bp. The length of the fragment may depend on the method used to detect the fragment, and is an approximation of its true length, plus or minus a few bases. It should however be taken into consideration that crossings between plants can result in certain markers being lost, so that the absence of a certain marker does not rule out the presence of the genetic element that confers resistance to disease and to which that marker is said to be linked. Primer extension codes as generally applied in AFLP analyses are shown in the list below, and as used herein (Source: Keygene, Wageningen, The Netherlands)

| Primer codes |
| --- |
| Extension Primercode |
| +0  00 |
| Extension Primercode |
| +1 |
| A 01 |
| C 02 |
| G 03 |
| T 04 |
| Extension Primercode |
| +2 |
| AA 11 |
| AC 12 |
| AG 13 |
| AT 14 |
| CA 15 |
| CC 16 |
| CG 17 |
| CT 18 |
| GA 19 |
| GC 20 |
| GG 21 |
| GT 22 |
| TA 23 |
| TC 24 |
| TG 25 |
| TT 26 |
| Extension Primercode |
| +3 |
| AAA 31 |
| AAC 32 |
| AAG 33 |
| AAT 34 |
| ACA 35 |
| ACC 36 |
| ACG 37 |
| ACT 38 |
| AGA 39 |
| AGC 40 |
| AGG 41 |
| AGT 42 |
| ATA 43 |
| ATC 44 |
| ATG 45 |
| ATT 46 |
| CAA 47 |
| CAC 48 |
| CAG 49 |
| CAT 50 |
| CCA 51 |
| CCC 52 |
| CCG 53 |
| CCT 54 |
| CGA 55 |
| CGC 56 |
| CGG 57 |
| CGT 58 |
| CTA 59 |
| CTC 60 |
| CTG 61 |
| CTT 62 |
| GAA 63 |
| GAC 64 |
| GAG 65 |
| GAT 66 |
| GCA 67 |
| GCC 68 |
| GCG 69 |
| GCT 70 |
| GGA 71 |
| GGC 72 |
| GGG 73 |

-continued

| Primer codes |
| --- |
| GGT 74 |
| GTA 75 |
| GTC 76 |
| GTG 77 |
| GTT 78 |
| TAA 79 |
| TAC 80 |
| TAG 81 |
| TAT 82 |
| TCA 83 |
| TCC 84 |
| TCG 85 |
| TCT 86 |
| TGA 87 |
| TGC 88 |
| TGG 89 |
| TGT 90 |
| TTA 91 |
| TTC 92 |
| TTG 93 |
| TTT 94 |

The inventors chose 'WSXP1030' (which is also known as 'Ns') for the initial marker studies because the pathology test results with SLCV on lines generated from 'WSXP1030' showed that they have very good resistance, better than the industry standards 'Topazio' and Sergio Garza's inbreds.

The analysis was done on 21 plants from an F2 of 'WSXP1030' crossed with a susceptible plant. The phenotyped plants were F3 generation plants. The F1 generated by this cross were self pollinated to produce an F2 generation and the resultant DNA was used in the AFLP analysis.

The twenty-one F3 individuals phenotyped for resistance were available for the Bulked Segregant Analysis (BSA) in combination with the AFLP technology. Identified candidate AFLP markers were validated on a panel of 95 phenotyped individuals.

4.1 Biological Material

Twenty-one squash individuals were phenotyped for the SLCV resistance and leaf samples thereof were obtained in duplicate. Eleven of the individuals were SLCV phenotyped sensitive and ten were phenotyped SLCV resistant.

Further leaf samples were used from a panel of germplasm samples for validation of the candidate AFLP markers linked to the SLCV resistance.

4.2 Bulk Segregation Analysis (BSA) and First Verification of Candidate Markers

The AFLP protocol used is described by Vos et al. (1995), starting with DNA extraction from the duplicate samples of the twenty-one phenotyped individuals that could be used for bulk composition. This DNA was digested with the restriction enzymes EcoR and Mse1.

To assess the quality of these samples for the generation of AFLP fingerprints, a test primers combination (PC) was run: E14/M49. In this test-PC fingerprint one candidate marker for SLCV resistance was found (electrophoretic mobility 88). Based on phenotype and fingerprint quality, samples were selected for composing the SLCV resistant and sensitive bulks of 10 individuals each for the R (resistant) and S (sensitive) bulks, respectively (Table 6).

TABLE 6

Bulk Analysis Using AFLP Markers

| In bulk | Phenotype | PC sample | AFLP+ in mobility PC | R 161 E12/M49 | R 115 E18/M62 | S 433 E12/M51 | R 114 E18/M54 | R 92 E15/M61 | R 310 E15/M60 | S 206 E14/M58 | R 177 E12/M58 | R 82 E12/M49 | R 378 E14/M58 | S 60 E18/M54 | R 134 E23/M60 |
|---|---|---|---|---|---|---|---|---|---|---|---|---|---|---|---|
| R | R | VC04 | | A | A | A | A | A | A | A | A | A | A | A | A |
| R | R | VC05 | | A | A | A | A | A | A | A | A | A | A | A | A |
| R | R | VC06 | | A | A | A | A | A | A | A | A | A | A | A | A |
| R | R | VC08 | | A | A | A | A | A | A | A | A | A | A | A | A |
| R | R | VC09 | | A | H | A | A | A | A | A | A | A | A | A | A |
| R | R | VC12 | | A | H | A | A | A | A | A | A | A | U | A | A |
| R | R | VC13 | | A | H | A | A | A | A | A | A | A | A | A | A |
| R | R | VC18 | | A | H | A | A | A | A | A | A | A | A | A | A |
| R | R | VC14 | | B | H | A | A | A | A | A | A | A | A | A | A |
| R | R | VC16 | | B | B | D | B | B | B | B | B | B | B | A | A |
| S | S | VC01 | | B | B | B | B | B | B | B | B | B | B | B | B |
| S | S | VC02 | | A | B | B | B | B | B | B | B | B | B | B | B |
| S | S | VC03 | | B | B | B | U | B | B | B | B | B | B | U | B |
| S | S | VC07 | | B | B | B | U | B | B | B | B | B | B | U | B |
| S | S | VC10 | | B | B | B | B | B | B | B | B | B | B | B | B |
| S | S | VC11 | | B | B | B | B | B | B | B | B | B | B | B | B |
| S | S | VC15 | | B | B | B | B | B | B | B | B | B | B | B | B |
| S | S | VC17 | | B | B | B | B | B | B | B | B | B | B | B | B |
| S | S | VC19 | | B | B | B | B | B | B | B | B | B | B | B | B |
|  | S | VC20 | | B | B | B | B | B | B | B | B | B | B | B | U |
| S | S | VC21 | | B | B | B | B | B | B | B | B | B | B | B | B |
| S |  | Sbulk | | B | B | B | U | B | B | B | B | B | B | U | B |
| R |  | Rbulk | | A | H | A | A | A | A | A | A | A | A | A | A |

| In bulk | Phenotype | PC sample | AFLP+ in mobility PC | R 49 E12/M62 | R 376 E12/M62 | R 238 E18/M62 | S 212 E23/M48 | S 138 E26/M48 | R 179 E26/M48 | S 180 E26/M48 | S 124 E26/M48 | S 88 E14/M49 | S 256 E23/M60 | S 60 E15/M61 | R 403 E18/M62 |
|---|---|---|---|---|---|---|---|---|---|---|---|---|---|---|---|
| R | R | VC04 | | A | A | A | A | A | A | A | A | A | A | A | A |
| R | R | VC05 | | A | A | A | A | A | A | A | A | A | A | A | A |
| R | R | VC06 | | A | A | A | A | A | A | A | A | A | A | A | A |
| R | R | VC08 | | U | U | A | A | A | A | A | A | A | A | A | A |
| R | R | VC09 | | A | A | A | A | A | A | A | A | A | A | A | A |
| R | R | VC12 | | A | A | A | A | U | U | U | U | A | H | B | B |
| R | R | VC13 | | A | A | A | A | A | A | A | A | A | A | A | A |
| R | R | VC18 | | A | A | A | A | A | A | A | A | A | A | A | A |
| R | R | VC14 | | A | U | A | A | A | A | A | A | A | A | A | C |
| R | R | VC16 | | A | A | A | A | A | A | A | A | A | A | A | A |

TABLE 6-continued

Bulk Analysis Using AFLP Markers

| | | | | | | | | | | | | | | |
|---|---|---|---|---|---|---|---|---|---|---|---|---|---|---|
| S | S | VC01 | B | B | B | B | B | B | B | B | B | B | B | B |
| S | S | VC02 | B | B | B | B | B | B | B | H | H | B | B | B |
| S | S | VC03 | B | B | B | B | B | B | B | B | B | B | B | B |
| S | S | VC07 | B | B | B | B | B | B | B | C | H | B | B | C |
| S | S | VC10 | B | U | B | B | B | B | B | B | B | B | B | B |
| S | S | VC11 | B | B | B | B | B | B | B | B | B | H | B | B |
| S | S | VC15 | B | B | B | B | B | B | B | B | C | B | B | B |
| S | S | VC17 | B | B | B | B | B | B | B | B | B | B | B | B |
| S | S | VC19 | B | B | B | B | B | B | B | B | B | B | B | B |
| | S | VC20 | B | B | B | B | B | B | B | B | B | U | B | B |
| S | S | VC21 | B | B | B | B | B | B | B | B | H | B | B | B |
| S | | Sbulk | B | B | B | B | B | B | B | B | | B | B | B |
| R | | Rbulk | A | A | A | A | A | A | A | A | A | A | A | A |

A = homozygous resistant P1 (parent 1)
B = homozygous susceptible P2 (parent 2)
H = heterozygous
C = between H and B
D = between H and A
U = Unknown 84 primers combinations were screened on the two bulks using EcoR1+2 and Mse1+3 combinations. As a result, 42 markers between the two bulks were found. Based on these BSA results 12 primers combinations (E12/M49, E18/M62, E12/M51, E18/M54, E15/M61, E15/M60, E14/M58, E12/M58, E23/M60, E12/M62, E23/M48, E26/M48), were chosen and screened on the 21 phenotyped individuals. This screening resulted in the identification of 23 candidate markers that show correlation with the expected SLCV phenotype.

The scores of a total of 24 markers (including the marker from the test PC) from 13 primers combinations are available for the 21 individuals (Table 6). Of these, nine (E18/M54-60, E23/M60-134, E12/M62-49, E12/M62-376, E18/M62-238, E23/M48-212, E26/M48-138, E26/M48-179, E26/M48-180) were in complete agreement with the provided phenotypes. The other ones show "H" or "C", meaning they are heterozygous or 'in between". These can't be used further, as they are not "clear cut" markers. Please note that a "U" (unknown) is more preferable than a "H", "C" or "B".

4.3 Validation of Candidate Markers from Four PCs on a Panel of 95 Germplasm Lines Further leaf samples from a panel of phenotyped germplasm lines were received for validation of the most promising candidate markers for SLCV resistance. From the results of the screening on the 21 individuals for bulk composition, four primer combinations (E18/M62, E12/M62, E23/M48, E26/M48) were selected and used to screen this panel. The four primer combinations together contain ten candidate markers of which eight had "perfect fit" in the panel of the 21 first individuals.

The scores of these eight markers in the individuals of the validation panel are reported in Table 7.

TABLE 7

Bulk Analysis on a panel of 95 germplasm lines

| Phenotype | marker sample | E12/M62-047.39\|P1 | E12/M62-377.23\|P1 | E18/M62-237.22\|P1 | E23/M48-212.18\|P2 | E26/M48-138.06\|P2 | E26/M48-179.61\|P1 | E26/M48-180.51\|P2 | E26/M48-123.85\|P2 |
|---|---|---|---|---|---|---|---|---|---|
| R | 5901 | A | A | A | A | A | A | A | A |
| R | 5903 | A | A | A | A | A | A | A | A |
| R | 5904 | A | A | A | A | A | A | A | A |
| R | 5906 | A | A | A | B | B | A | A | B |
| R | 5907 | A | A | A | A | A | A | A | A |
| R | 5909 | A | A | A | A | A | A | A | A |
| R | 5911 | B | B | B | A | A | A | A | A |
| R | 5912 | A | A | B | A | A | A | A | A |
| R | 5913 | A | A | B | A | A | A | A | A |
| R | 5915 | A | A | A | A | A | A | A | A |
| R | 5916 | A | A | A | A | A | A | A | A |
| R | 5918 | A | A | A | A | A | A | A | A |
| R | 5919 | A | A | A | A | A | A | A | A |
| R | 5921 | A | A | A | A | A | A | A | A |
| R | 5923 | A | A | B | A | A | A | A | A |
| R | 5924 | A | A | A | A | A | A | A | A |
| R | 5926 | A | A | A | A | A | A | A | A |
| R | 5929 | A | A | H | A | A | A | A | A |
| R | 5931 | A | A | A | A | A | A | A | A |
| R | 5933 | A | A | A | A | A | A | A | A |
| R | 5935 | A | A | A | D | A | A | A | A |
| R | 5937 | A | A | H | A | A | A | A | A |
| R | 5939 | A | A | A | A | A | A | A | A |
| R | 5941 | A | A | A | A | A | A | A | A |
| R | 5942 | A | A | A | A | A | A | A | A |
| R | 5944 | A | D | A | A | A | A | A | A |
| R | 5945 | A | A | A | A | A | A | A | A |
| R | 5947 | A | A | A | A | A | A | A | A |
| R | 5952 | A | A | A | A | A | A | A | A |
| R | 5953 | A | A | A | A | A | A | A | A |
| R | 5955 | A | A | A | A | A | A | A | A |
| R | 5958 | A | A | B | D | A | A | A | A |
| R | 5960 | A | D | A | D | A | A | A | A |
| R | 5961 | B | B | B | B | B | B | B | B |
| R | 5963 | B | B | B | B | B | B | B | B |
| R | 5964 | B | B | B | B | A | B | B | B |
| R | 5965 | B | B | B | B | B | B | B | B |
| R | 5966 | B | B | B | B | B | B | B | B |

TABLE 7-continued

Bulk Analysis on a panel of 95 germplasm lines

| | | | | | | | | | |
|---|---|---|---|---|---|---|---|---|---|
| R | 5967 | B | B | B | B | B | B | B | B |
| R | 5968 | B | B | B | B | B | B | B | B |
| R | 5970 | B | A | B | A | A | A | A | A |
| R | 5978 | A | A | D | A | A | A | A | A |
| R | 5979 | A | B | B | A | A | A | A | A |
| R | 5980 | A | A | A | A | A | A | A | A |
| R | 5981 | A | A | A | A | A | A | A | A |
| S | 5902 | B | B | B | B | B | B | B | B |
| S | 5905 | B | B | B | B | B | B | B | B |
| S | 5908 | B | B | B | A | B | B | B | B |
| S | 5910 | B | B | B | A | B | B | B | B |
| S | 5914 | B | B | B | B | B | B | B | B |
| S | 5917 | B | B | B | B | B | B | B | B |
| S | 5920 | B | B | B | A | B | B | B | B |
| S | 5922 | B | B | B | B | B | B | B | B |
| S | 5925 | B | B | B | B | B | B | B | B |
| S | 5927 | B | B | B | B | B | B | B | B |
| S | 5928 | B | B | B | B | B | B | B | B |
| S | 5930 | B | B | B | B | B | B | B | B |
| S | 5932 | B | B | B | B | B | B | B | B |
| S | 5934 | B | B | B | A | B | B | B | B |
| S | 5936 | B | B | B | B | B | B | B | B |
| S | 5938 | B | B | B | B | B | B | B | B |
| S | 5940 | B | B | B | A | B | B | B | B |
| S | 5943 | B | B | B | B | B | B | B | B |
| S | 5946 | C | H | C | B | B | B | B | B |
| S | 5949 | B | B | B | B | B | B | B | B |
| S | 5951 | B | B | B | B | B | B | B | B |
| S | 5954 | B | B | B | B | B | B | B | B |
| S | 5956 | B | B | B | B | B | B | B | B |
| S | 5957 | B | B | B | B | B | B | B | B |
| S | 5959 | U | U | U | U | U | U | U | U |
| S | 5962 | B | B | B | A | B | B | B | B |
| S | 5971 | B | B | B | B | B | B | B | B |
| S | 5972 | B | B | B | A | B | B | B | B |
| S | 5973 | B | B | B | B | B | B | B | B |
| S | 5974 | B | B | B | B | B | B | B | B |
| S | 5975 | B | B | B | B | B | B | B | B |
| S | 5976 | B | B | B | B | B | B | B | B |
| S | 5977 | B | B | B | B | B | B | B | B |
| S | 5982 | B | B | B | B | B | B | B | B |
| S | 5983 | B | B | B | B | B | B | B | B |
| S | 5984 | B | B | B | B | B | B | B | B |
| S | 5985 | B | B | B | B | B | B | B | B |
| S | 5986 | B | B | B | B | B | B | B | B |
| S | 5987 | B | B | B | B | B | B | B | B |
| S | 5988 | B | B | B | B | B | B | B | B |
| S | 5989 | B | B | B | D | B | B | B | B |
| S | 5990 | B | B | B | B | B | B | B | B |
| S | 5991 | B | B | B | B | B | B | B | B |
| S | 5992 | B | B | B | B | B | B | B | B |
| S | 5993 | B | B | B | B | B | B | B | B |

TABLE 7-continued

Bulk Analysis on a panel of 95 germplasm lines

| | | | | | | | | | |
|---|---|---|---|---|---|---|---|---|---|
| S | 5982 | B | B | B | B | B | B | B | B |
| S | 5983 | B | B | B | B | B | B | B | B |
| S | 5984 | B | B | B | B | B | B | B | B |
| S | 5985 | B | B | B | B | B | B | B | B |
| S | 5986 | B | B | B | B | B | B | B | B |
| S | 5987 | B | B | B | B | B | B | B | B |
| S | 5988 | B | B | B | B | B | B | B | B |
| S | 5989 | B | B | B | D | B | B | B | B |
| S | 5990 | B | B | B | B | B | B | B | B |
| S | 5991 | B | B | B | B | B | B | B | B |
| S | 5992 | B | B | B | B | B | B | B | B |
| S | 5993 | B | B | B | B | B | B | B | B |
| S | 5994 | B | B | B | B | B | B | B | B |
| S | 5995 | B | B | B | B | B | B | B | B |
| S | 5995 | B | B | B | B | B | B | B | B |
| S | 5995 | D | H | H | B | B | B | B | B |
| | | 2 | TOO MANY | | 2 | | 1 | | 2 |

A = homozygous resistant P1 (parent 1)
B = homozygous susceptible P2 (parent 2)
H = heterozygous
C = between H and B
D = between H and A
U = Unknown Primers used to amplicfy the molecular markers that link to the resistance are shown in Table 8 below.

TABLE 8

Primers for AFLP Marks

| AFLP PRIMER COMBINATION | Forward sequence | Reverse sequence |
|---|---|---|
| E12/M49 | GACTGCGTACCAATTCAC (SEQ ID NO.: 1) | GATGAGTCCTGAGTAACAG (SEQ ID NO.: 2) |
| E12/M51 | GACTGCGTACCAATTCAC (SEQ ID NO.: 3) | GATGAGTCCTGAGTAACCA (SEQ ID NO.: 4) |
| E12/M58 | GACTGCGTACCAATTCAC (SEQ ID NO.: 5) | GATGAGTCCTGAGTAACGT (SEQ ID NO.: 6) |
| E12/M62 | GACTGCGTACCAATTCAC (SEQ ID NO.: 7) | GATGAGTCCTGAGTAACTT (SEQ ID NO.: 8) |
| E14/M49 | GACTGCGTACCAATTCAT (SEQ ID NO.: 9) | GATGAGTCCTGAGTAACAG (SEQ ID NO.: 10) |
| E14/M58 | GACTGCGTACCAATTCAT (SEQ ID NO.: 11) | GATGAGTCCTGAGTAACGT (SEQ ID NO.: 12) |
| E15/M60 | GACTGCGTACCAATTCCA (SEQ ID NO.: 13) | GATGAGTCCTGAGTAACTC (SEQ ID NO.: 14) |
| E15/M61 | GACTGCGTACCAATTCCA (SEQ ID NO.: 15) | GATGAGTCCTGAGTAACTG (SEQ ID NO.: 16) |
| E18/M54 | GACTGCGTACCAATTCCT (SEQ ID NO.: 17) | GATGAGTCCTGAGTAACCT (SEQ ID NO.: 18) |
| E18/M62 | GACTGCGTACCAATTCCT (SEQ ID NO.: 19) | GATGAGTCCTGAGTAACTT (SEQ ID NO.: 20) |
| E23/M48 | GACTGCGTACCAATTCTA (SEQ ID NO.: 21) | GATGAGTCCTGAGTAACAC (SEQ ID NO.: 22) |
| E23/M60 | GACTGCGTACCAATTCTA (SEQ ID NO.: 23) | GATGAGTCCTGAGTAACTC (SEQ ID NO.: 24) |

TABLE 8-continued

Primers for AFLP Marks

| AFLP PRIMER COMBINATION | Forward sequence | Reverse sequence |
|---|---|---|
| E26/M48 | GACTGCGTACCAATTCTT (SEQ ID NO.: 25) | GATGAGTCCTGAGTAACAC (SEQ ID NO.: 26) |

The observed phenotype of each plant of the validation panel was compared to the genotype generated with the scoring of the markers. From this analysis, it could be concluded that the markers E26/M48-179 and E26/M48-180 have the best predictive value for the SLCV resistance. Also of interest are markers E26/M48-138, E26/M48-123 and E12/M62-047.

Several germplasm derived from a different source of resistance to SLCV, identified by Sergio Garza of the Universidad de Sonora in Hermosillo, Mexico (USON) and released to seed companies in 1998 as an open pollinated variety of gray zucchini (c. pepo) were included in the panel as samples '5961', '5963', '5964', '5965', '5966', '5667' and '5968'. The genotype results confirm that the present inventors have identified a new resistance to SLCV, different from the one derived from the USON released material.

Example 5

Material Development and Further Analysis

The additional marker information was utilized for selections from internal advanced material from several types of squashes, showing that the gene of resistance can be transmitted and followed by the markers from one generation to the next, as well as from one genetic background to another.

Approximately 50 lines ranging from F4 to F8 were tested for their resistance. Many are related sister lines, but at least 25 different parents have been created. More than 50 experimental hybrids were created for testing, in grey zucchini, green zucchini and white squash genetic backgrounds. Their DNA was also tested for the resistance gene.

The additional marker information was also collected on external and commercial material including both Sergio Garza's material and all the commercial varieties that are asserted to be SLCV resistant. Lists of applicable lines are provided elsewhere herein.

The internal material analyzed was advanced material phenotyped as resistant, at various levels of development, in various genetic backgrounds.

A list of current cultivars developed by external sources was tested and the results are provided in Table 9.

To integrate the resistance gene slc-2 into other backgrounds, the resistance donor line (e.g., 'Ns', 'CT3' or 'CT4') was crossed to a recipient line (e.g., the external material or internal material mentioned above and in Table 9), and resultant hybrid plants are either selfed for several generations (e.g., F4, F5, and F6), or backcrossed to recipient lines for one or two generations, and then selfed for several generations (e.g., BC1F4, BC1F5, BC1F6, BC1F7; BC2F4, BC2F5, BC2F6, BC2F7). These materials can then be tested against SLCV infection, and resistant new lines will be selected. The molecular markers identified herein can be used to facilitate the selection of new lines that are SLCV resistant.

As shown in Table 9, the results indicate that the resistance gene can be transferred from one generation to the next in a given genetic background, transferred in different backgrounds of a same zucchini type, and/or transferred in different zucchini types through appropriate breeding methods. The results also indicate that the resistance gene slc-2 is linked to SLCV resistance, is a new source of SLCV resistance and that it is not presently found in commercially available SLCV resistant cucurbit plants.

TABLE 9

Materials Tested

| NAME | ORIGINE | BACKGROUND | LEVEL | SLCV | E12/M62-047.39|P1 | E12/M62-377.23|P1 | E26/M48-123.85|P1 | E26/M48-138.06|P2 | E26/M48-129.66|P2 | E26/M48-180.33|P2 | COMMENTS |
|---|---|---|---|---|---|---|---|---|---|---|---|
| DEPREDATOR | SEMINIS | GREY | hybrid | R2 | B | B | B | B | B | B | The resistance gene of the present invention is not present in commercial materials available so far, nor in the materials developed by USON. |
| SHOROUQ | SYNGENTA | WHITE BULBOUS | hybrid | R2 | B | B | B | B | B | B | |
| TOPAZIO | SYNGENTA | GREY | hybrid | R2 | B | B | B | B | B | B | |
| CUARZO | SYNGENTA | GREY | hybrid | R2 | B | B | B | B | B | B | |
| JASPER | DPSEEDS | GREEN ZUCCHINI | hybrid | R2 | B | B | B | B | B | B | The resistance gene of the present invention is different from the resistance gene(s) available so far. |
| OBSIDIAN | DPSEEDS | GREEN ZUCCHINI | hybrid | R2 | B | B | B | B | B | B | |
| GREYBEARD | DPSEEDS | GREY | hybrid | R2 | B | B | B | B | B | B | |
| USON lines 211 | GARZA | GREY | inbred | R2 | B | B | B | B | B | B | |
| USON lines 212 | GARZA | GREY | inbred | R2 | B | B | B | B | B | B | |
| USON lines 214 | GARZA | GREY | inbred | R2 | B | B | B | B | | | |
| USON lines 215 | GARZA | GREY | inbred | R2 | B | B | B | B | B | B | |
| USON lines 232 | GARZA | GREY | inbred | R2 | B | B | B | B | B | B | |
| USON lines 253 | GARZA | GREY | inbred | R2 | B | B | B | B | B | B | |
| USON lines 262 | GARZA | GREY | inbred | R2 | B | B | B | B | B | B | |
| USON lines 264 | GARZA | GREY | inbred | R2 | B | B | B | B | B | B | |
| ZY62932NsCMO9 | HM | GREEN ZUCCHINI | F5 | R | | | | | | | |
| ZY62932NsCMO9 | HM | GREEN ZUCCHINI | F6 | R | U | | | | | | |
| ZY62932NsCMO9 | HM | GREEN ZUCCHINI | F7 | R | | | | | | | |
| NsCMVZYO34 | HM | GREEN ZUCCHINI | F4 | R | | | | | | | Transfert in different green zucc background |
| NsCMVZYO34 | HM | GREEN ZUCCHINI | F5 | R | | | | | | | |
| NsCMVZYO34 | HM | GREEN ZUCCHINI | F6 | R | | | | | | | Gene transferred from F5 to F7 |
| NsCMVZYO34 | HM | GREEN ZUCCHINI | F7 | R | | | | | | | |
| NsCMC59CMQ | HM | GREY | F4 | R | | | | | | | Transfert in different green zucc background |
| NsCMC59CMQ | HM | GREY | F5 | R | | | | | | | Gene transferred from F4 to F6 |
| NsCMC59CMQ | HM | GREY | F6 | R | | | | | | | |
| NsCMVZ133 | HM | GREY | BC2F4 | R | | | | | | | Transfert in different grey zucc background |
| NsCMVZ133 | HM | GREY | BC2F6 | R | | | | | | | Gene transferred from BC2F4 to BC2F8 |
| NsCMVZ133 | HM | GREY | BC2F7 | R | | | | | | | |

TABLE 9-continued

Materials Tested

| Name | Type | Color | Generation | Status | Notes |
|---|---|---|---|---|---|
| NsCMVZ133 | HM | GREY | BC2F8 | R | |
| NsCMC59 | HM | GREY | F4 | R | Gene transfered from F4 to F7 |
| NsCMC59 | HM | GREY | F5 | R | |
| NsCMC59 | HM | GREY | F6 | R | |
| NsCMC59 | HM | GREY | F7 | R | |
| NsCMVO9 | HM | GREY | F4 | R | Gene transfered from F4 to F7 |
| NsCMVO9 | HM | GREY | F5 | R | |
| NsCMVO9 | HM | GREY | F6 | R | |
| NsCMVO9 | HM | GREY | F7 | R | |
| NsC712 | HM | GREY | BC1F5 | R | Gene transfered from BC1F5 to BC1F7 |
| NsC712 | HM | GREY | BC1F6 | R | |
| NsC712 | HM | GREY | BC1F7 | R | |
| NsZ29 | HM | WHITE | OCF5 | R | Transfert in different white zucc background |
| ZY11DNsC712 | HM | WHITE | F5 | R | |
| CMVZ13 | HM | GREY | | S | Absence of marker in all susceptible materials, regardless of types and backgrounds |
| HURAKAN | HM | GREY | hybrid | S | |
| C59 | HM | GREY | inbred | S | |
| zucchini elite | HM | GREEN | | S | |
| ZY62932 | HM | GREEN | F9 | S | |
| O9 | HM | GREEN | inbred | S | |
| ZY11D | HM | WHITE | inbred | S | |
| SSXP4709 | HM | GREY | homozygous resistant hybrids | | Gene at homozygous stage, for creation of R hybrid |
| SSXP4676 | HM | GREY | | | |
| SSXP4672 | HM | GREY | | | |

Legende:
A = Resistant
B = Susceptible
U = Unknown
R stands for slc-2 gene associated resistance;
R2 stands for resistance which is different from slc-2 gene associated resistance;

DEPOSIT INFORMATION

A deposit of the squash seed of this invention is maintained by Harris Moran Seed Company Davis Research Station, 9241 Mace Boulevard, Davis Calif. 95616. In addition, a sample of the squash seed of this invention has been deposited with the National Collections of Industrial, Food and Marine Bacteria (NCIMB), 23 St Machar Drive, Aberdeen, Scotland, AB24 3RY, United Kingdom.

To satisfy the enablement requirements of 35 U.S.C. §112, and to certify that the deposit of the seeds of the present invention meets the criteria set forth in 37 C.F.R. §§1.801-1.809, Applicants hereby make the following statements regarding the deposited squash seed N9N030 (deposited as NCIMB Accession No. 41728 on Jun. 18, 2010):

1. During the pendency of this application, access to the invention will be afforded to the Commissioner upon request;
2. Upon granting of the patent the strain will be available to the public under conditions specified in 37 CFR 1.808;
3. The deposit will be maintained in a public repository for a period of 30 years or 5 years after the last request or for the enforceable life of the patent, whichever is longer;
4. The viability of the biological material at the time of deposit will be tested; and
5. The deposit will be replaced if it should ever become unavailable.

Access to this deposit will be available during the pendency of this application to persons determined by the Commissioner of Patents and Trademarks to be entitled thereto under 37 C.F.R. §1.14 and 35 U.S.C. §122. Upon allowance of any claims in this application, all restrictions on the availability to the public of the variety will be irrevocably removed by affording access to a deposit of at least 2,500 seeds of the same seed source with the NCIMB.

Unless defined otherwise, all technical and scientific terms herein have the same meaning as commonly understood by one of ordinary skill in the art to which this invention belongs. Although any methods and materials, similar or equivalent to those described herein, can be used in the practice or testing of the present invention, the preferred methods and materials are described herein. All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES

1. Whitham, S. et al. The product of the tobacco mosaic virus resistance gene N: similarity to toll and the interleukin-1 receptor. Cell 78, 1101-1115 (1994).
2. Bendahmane, A., Kanyuka, K. & Baulcombe, D. C. The Rx gene from potato controls separate virus resistance and cell death responses. Plant Cell 11, 781-791 (1999).
3. Bendahmane, A., Querci, M., Kanyuka, K. & Baulcombe, D. C. Agrobacterium transient expression system as a tool for the isolation of disease resistance genes: application to the Rx2 locus in potato. Plant J. 21, 73-81 (2000).
4. Cooley, M. B., Pathirana, S., Wu, H.-J., Kachroo, P. & Klessig, D. F. Members of the Arabidopsis HRT/RPP8 family of resistance genes confer resistance to both viral and oomycete pathogens. Plant Cell 12, 663-676 (2000).
5. Takahashi, H. et al. Arabidopsis thaliana RPP8/HRT family resistance gene, conferring resistance to cucumber mosaic virus requires salicylic acid, ethylene and a novel signal transduction mechanism. Plant J. 32, 655-667 (2002).
6. Spassova, M. I. et al. The tomato gene Sw5 is a member of the coiled coil, nucleotide binding, leucine-rich repeat class of plant resistance genes and confers resistance to TSWV in tobacco. Mol. Breed. 7, 151-161 (2001).
7. Vidal, S., Cabrera, H., Andersson, R. A., Fredriksson, A. & Valkonen, J. P. Potato gene Y-1 is an N gene homolog that confers cell death upon infection with potato virus Y. Mol. *Plant Microbe Interact.* 15, 717-727 (2002).
8. Lanfermeijer, F. C., Dijkhuis, J., Sturre, M. J., de Haan, P. & Hille, J. Cloning and characterization of the durable tomato mosaic virus resistance gene Tm-22 from Cycopersicon esculentum. *Plant Mol. Biol.* 52, 1037-1049 (2003).

---

The invention claimed is:

1. A method of identifying a Squash Leaf Curl Virus (SLCV) resistant *Cucurbita pepo* plant by identifying one or more genetic loci linked with one or more genetic markers, wherein the one or more genetic loci are linked with a recessive allele of a slc-2 gene for resistance to Squash Leaf Curl Virus (SLCV), said recessive allele being present in the seeds deposited as NCIMB Accession No. 41728, the method comprising:

(i) detecting the presence of the one or more genetic loci in the plant by isolating nucleic acid comprising the one or more genetic markers linked with the genetic locus, wherein the genetic locus localizes to a chromosome interval flanked on either side by the one or more genetic markers; and (ii) screening the isolated nucleic acid for the presence of the one or more genetic markers, thereby identifying the plant comprising the one or more genetic loci;

wherein the recessive allele of the slc-2 gene was originally obtained from *Cucurbita moschata*.

2. The method of claim 1, wherein the identification is conducted using a whole plant, a plant organ, a plant seed, or a plant cell.

3. The method of claim 1, wherein the method further comprises constructing a genetic linkage map of said plant using the genetic marker.

4. The method of claim 1, wherein the genetic marker is located within the chromosomal interval defined by two molecular markers selected from the group consisting of E18/M54-60, E23/M60-134, E12/M62-49, E12/M62-376, E18/M62-238, E23/M48-212, E26/M48-138, E26/M48-179, and E26/M48-180.

* * * * *

SEQUENCE LISTING

```
<160> NUMBER OF SEQ ID NOS: 26

<210> SEQ ID NO 1
<211> LENGTH: 18
<212> TYPE: DNA
<213> ORGANISM: Artificial Sequence
<220> FEATURE:
<223> OTHER INFORMATION: E12/M49 F

<400> SEQUENCE: 1
gactgcgtac caattcac                                                18

<210> SEQ ID NO 2
<211> LENGTH: 19
<212> TYPE: DNA
<213> ORGANISM: Artificial Sequence
<220> FEATURE:
```

```
<223> OTHER INFORMATION: E12/M49 R

<400> SEQUENCE: 2
gatgagtcct gagtaacag                                                    19

<210> SEQ ID NO 3
<211> LENGTH: 18
<212> TYPE: DNA
<213> ORGANISM: Artificial Sequence
<220> FEATURE:
<223> OTHER INFORMATION: E12/M51 F

<400> SEQUENCE: 3
gactgcgtac caattcac                                                     18

<210> SEQ ID NO 4
<211> LENGTH: 19
<212> TYPE: DNA
<213> ORGANISM: Artificial Sequence
<220> FEATURE:
<223> OTHER INFORMATION: E12/M51 R

<400> SEQUENCE: 4
gatgagtcct gagtaacca                                                    19

<210> SEQ ID NO 5
<211> LENGTH: 18
<212> TYPE: DNA
<213> ORGANISM: Artificial Sequence
<220> FEATURE:
<223> OTHER INFORMATION: E12/M58 F

<400> SEQUENCE: 5
gactgcgtac caattcac                                                     18

<210> SEQ ID NO 6
<211> LENGTH: 19
<212> TYPE: DNA
<213> ORGANISM: Artificial Sequence
<220> FEATURE:
<223> OTHER INFORMATION: E12/M58 R

<400> SEQUENCE: 6
gatgagtcct gagtaacgt                                                    19

<210> SEQ ID NO 7
<211> LENGTH: 18
<212> TYPE: DNA
<213> ORGANISM: Artificial Sequence
<220> FEATURE:
<223> OTHER INFORMATION: E12/M62 F

<400> SEQUENCE: 7
gactgcgtac caattcac                                                     18

<210> SEQ ID NO 8
<211> LENGTH: 19
<212> TYPE: DNA
<213> ORGANISM: Artificial Sequence
<220> FEATURE:
<223> OTHER INFORMATION: E12/M62 R

<400> SEQUENCE: 8
gatgagtcct gagtaactt                                                    19

<210> SEQ ID NO 9
```

```
<211> LENGTH: 18
<212> TYPE: DNA
<213> ORGANISM: Artificial Sequence
<220> FEATURE:
<223> OTHER INFORMATION: E14/M49 F

<400> SEQUENCE: 9
gactgcgtac caattcat                                                 18

<210> SEQ ID NO 10
<211> LENGTH: 19
<212> TYPE: DNA
<213> ORGANISM: Artificial Sequence
<220> FEATURE:
<223> OTHER INFORMATION: E14/M49 R

<400> SEQUENCE: 10
gatgagtcct gagtaacag                                                19

<210> SEQ ID NO 11
<211> LENGTH: 18
<212> TYPE: DNA
<213> ORGANISM: Artificial Sequence
<220> FEATURE:
<223> OTHER INFORMATION: E14/M58 F

<400> SEQUENCE: 11
gactgcgtac caattcat                                                 18

<210> SEQ ID NO 12
<211> LENGTH: 19
<212> TYPE: DNA
<213> ORGANISM: Artificial Sequence
<220> FEATURE:
<223> OTHER INFORMATION: E14/M58 R

<400> SEQUENCE: 12
gatgagtcct gagtaacgt                                                19

<210> SEQ ID NO 13
<211> LENGTH: 18
<212> TYPE: DNA
<213> ORGANISM: Artificial Sequence
<220> FEATURE:
<223> OTHER INFORMATION: E15/M60 F

<400> SEQUENCE: 13
gactgcgtac caattcca                                                 18

<210> SEQ ID NO 14
<211> LENGTH: 19
<212> TYPE: DNA
<213> ORGANISM: Artificial Sequence
<220> FEATURE:
<223> OTHER INFORMATION: E15/M60 R

<400> SEQUENCE: 14
gatgagtcct gagtaactc                                                19

<210> SEQ ID NO 15
<211> LENGTH: 18
<212> TYPE: DNA
<213> ORGANISM: Artificial Sequence
<220> FEATURE:
<223> OTHER INFORMATION: E15/M61 F

<400> SEQUENCE: 15
```
gactgcgtac caattcca				18

<210> SEQ ID NO 16
<211> LENGTH: 19
<212> TYPE: DNA
<213> ORGANISM: Artificial Sequence
<220> FEATURE:
<223> OTHER INFORMATION: E15/M61 R

<400> SEQUENCE: 16
gatgagtcct gagtaactg				19

<210> SEQ ID NO 17
<211> LENGTH: 18
<212> TYPE: DNA
<213> ORGANISM: Artificial Sequence
<220> FEATURE:
<223> OTHER INFORMATION: E18/M54 F

<400> SEQUENCE: 17
gactgcgtac caattcct				18

<210> SEQ ID NO 18
<211> LENGTH: 19
<212> TYPE: DNA
<213> ORGANISM: Artificial Sequence
<220> FEATURE:
<223> OTHER INFORMATION: E18/M54 R

<400> SEQUENCE: 18
gatgagtcct gagtaacct				19

<210> SEQ ID NO 19
<211> LENGTH: 18
<212> TYPE: DNA
<213> ORGANISM: Artificial Sequence
<220> FEATURE:
<223> OTHER INFORMATION: E18/M62 F

<400> SEQUENCE: 19
gactgcgtac caattcct				18

<210> SEQ ID NO 20
<211> LENGTH: 19
<212> TYPE: DNA
<213> ORGANISM: Artificial Sequence
<220> FEATURE:
<223> OTHER INFORMATION: E18/M62 R

<400> SEQUENCE: 20
gatgagtcct gagtaactt				19

<210> SEQ ID NO 21
<211> LENGTH: 18
<212> TYPE: DNA
<213> ORGANISM: Artificial Sequence
<220> FEATURE:
<223> OTHER INFORMATION: E23/M48 F

<400> SEQUENCE: 21
gactgcgtac caattcta				18

<210> SEQ ID NO 22
<211> LENGTH: 19
<212> TYPE: DNA
<213> ORGANISM: Artificial Sequence
<220> FEATURE:

-continued

```
<223> OTHER INFORMATION: E23/M48 R

<400> SEQUENCE: 22
gatgagtcct gagtaacac                                            19

<210> SEQ ID NO 23
<211> LENGTH: 18
<212> TYPE: DNA
<213> ORGANISM: Artificial Sequence
<220> FEATURE:
<223> OTHER INFORMATION: E23/M60 F

<400> SEQUENCE: 23
gactgcgtac caattcta                                             18

<210> SEQ ID NO 24
<211> LENGTH: 19
<212> TYPE: DNA
<213> ORGANISM: Artificial Sequence
<220> FEATURE:
<223> OTHER INFORMATION: E23/M60 R

<400> SEQUENCE: 24
gatgagtcct gagtaactc                                            19

<210> SEQ ID NO 25
<211> LENGTH: 18
<212> TYPE: DNA
<213> ORGANISM: Artificial Sequence
<220> FEATURE:
<223> OTHER INFORMATION: E26/M48 F

<400> SEQUENCE: 25
gactgcgtac caattctt                                             18

<210> SEQ ID NO 26
<211> LENGTH: 19
<212> TYPE: DNA
<213> ORGANISM: Artificial Sequence
<220> FEATURE:
<223> OTHER INFORMATION: E26/M48 R

<400> SEQUENCE: 26
gatgagtcct gagtaacac                                            19
```